United States Patent
George et al.

(10) Patent No.: US 10,251,790 B2
(45) Date of Patent: *Apr. 9, 2019

(54) METHOD FOR EXTERNAL EAR CANAL PRESSURE REGULATION TO ALLEVIATE DISORDER SYMPTOMS

(71) Applicant: NOCIRA, LLC, Tempe, AZ (US)

(72) Inventors: David George, Scottsdale, AZ (US); David Brice Sullivan, Mechanicsburg, PA (US); George Buckler, Phoenix, AZ (US)

(73) Assignee: Nocira, LLC, Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/292,469

(22) Filed: May 30, 2014

(65) Prior Publication Data
US 2015/0000678 A1 Jan. 1, 2015

Related U.S. Application Data

(60) Provisional application No. 61/983,865, filed on Apr. 24, 2014, provisional application No. 61/863,317, (Continued)

(51) Int. Cl.
*A61F 11/12* (2006.01)
*A61H 9/00* (2006.01)
(Continued)

(52) U.S. Cl.
CPC .............. *A61F 11/12* (2013.01); *A61F 11/00* (2013.01); *A61F 11/08* (2013.01); *A61H 9/005* (2013.01);
(Continued)

(58) Field of Classification Search
CPC .......... A61F 11/00; A61F 11/08; A61F 11/10; A61F 2011/085; A61F 11/06–11/14;
(Continued)

(56) References Cited

U.S. PATENT DOCUMENTS 476,446 A 6/1892 Brothwell
841,146 A 1/1907 Hasbrouck
(Continued)

FOREIGN PATENT DOCUMENTS

AU 2004/238090 11/2004
CA 1136751 11/1982
(Continued)

OTHER PUBLICATIONS

Minen, MD, MPH, Mia; Tinnitus and Headache, Feb. 8, 2017, American Migraine Foundation, website page.*
(Continued)

*Primary Examiner* — Victoria J Hicks
*Assistant Examiner* — Michelle Lee
(74) *Attorney, Agent, or Firm* — Knobbe Martens Olson & Bear, LLP

(57) ABSTRACT

A method for external ear canal pressure regulation to alleviate one or more symptoms associated with a disorder or treat one or more disorders, the method including providing a fluid transfer device which generates a fluid flow of a fluid through an earplug, the earplug having an earplug external surface configured to sealably engage an external ear canal wall as a barrier between an external ear canal pressure and an ambient pressure; sealably engaging the earplug of the fluid transfer device with the external ear canal wall as the barrier between the external ear canal pressure and the ambient pressure; and operating the fluid transfer device to generate the fluid flow of the fluid through the earplug to achieve an external ear canal pressure differential between the external ear canal pressure and the ambient pressure effective to alleviate a disorder symptom or treat a disorder.

15 Claims, 10 Drawing Sheets

Related U.S. Application Data filed on Aug. 7, 2013, provisional application No. 61/841,111, filed on Jun. 28, 2013.

(51) Int. Cl.
*A61H 21/00* (2006.01)
*A61F 11/00* (2006.01)
*A61F 11/08* (2006.01)

(52) U.S. Cl.
CPC ......... *A61H 9/0007* (2013.01); *A61H 9/0071* (2013.01); *A61H 21/00* (2013.01); *A61F 2011/085* (2013.01); *A61F 2250/0013* (2013.01); *A61H 2201/0153* (2013.01); *A61H 2201/0207* (2013.01); *A61H 2201/0214* (2013.01); *A61H 2201/10* (2013.01); *A61H 2201/105* (2013.01); *A61H 2205/027* (2013.01)

(58) Field of Classification Search
CPC .... A61H 9/0071; A61H 9/005–9/0078; A61H 21/00; A42B 1/06; A42B 3/16–3/166
See application file for complete search history.

(56) References Cited

U.S. PATENT DOCUMENTS

| | | | |
|---|---|---|---|
| 2,176,366 A | 10/1939 | Smith | |
| 2,437,490 A | 3/1948 | Watson et al. | |
| 2,652,048 A | 9/1953 | Joers | |
| 3,757,769 A | 9/1973 | Arguimbau et al. | |
| 3,872,559 A | 3/1975 | Leight | |
| 4,002,161 A | 1/1977 | Klar et al. | |
| 4,133,984 A | 1/1979 | Akijama | |
| 4,160,449 A | 7/1979 | Wade | |
| 4,206,756 A | 6/1980 | Grossan | |
| 4,244,377 A | 1/1981 | Grams | |
| 4,289,143 A | 9/1981 | Canavesio et al. | |
| 4,325,386 A * | 4/1982 | Katz | A61B 5/411 600/546 |
| 4,349,083 A | 9/1982 | Bennett | |
| 4,472,342 A | 9/1984 | Carr | |
| 4,552,137 A | 11/1985 | Strauss | |
| 4,632,104 A | 12/1986 | Conrow | |
| 4,667,676 A | 5/1987 | Guinta | |
| 4,688,582 A | 8/1987 | Heller et al. | |
| 4,754,748 A | 7/1988 | Antowski | |
| 4,757,807 A | 7/1988 | Densert et al. | |
| 4,775,370 A | 10/1988 | Berry | |
| 4,809,708 A | 3/1989 | Geisler et al. | |
| 4,896,380 A | 1/1990 | Kamitani | |
| 4,896,679 A | 1/1990 | St. Pierre | |
| 4,964,769 A | 10/1990 | Hass | |
| 4,984,579 A | 1/1991 | Burgert et al. | |
| 5,024,612 A * | 6/1991 | van den Honert | A61F 11/00 604/36 |
| 5,105,822 A | 4/1992 | Stevens et al. | |
| 5,131,411 A | 7/1992 | Casali et al. | |
| 5,241,967 A | 9/1993 | Yasushi et al. | |
| 5,421,818 A * | 6/1995 | Arenberg | A61F 11/00 604/20 |
| 5,476,446 A | 12/1995 | Arenburg | |
| 5,483,027 A | 1/1996 | Krause | |
| 5,483,975 A | 1/1996 | Hirschenbain | |
| 5,488,961 A | 2/1996 | Adams | |
| 5,631,965 A | 5/1997 | Chang et al. | |
| 5,699,809 A | 12/1997 | Combs et al. | |
| 5,740,258 A | 4/1998 | Goodwin-Johansson | |
| 5,746,725 A | 5/1998 | Shalon et al. | |
| 5,755,234 A | 5/1998 | Mobley et al. | |
| 5,769,891 A | 6/1998 | Clayton | |
| 5,776,179 A | 7/1998 | Ren et al. | |
| 5,819,745 A | 10/1998 | Mobley et al. | |
| 5,865,183 A * | 2/1999 | Hirschebain | A61F 11/08 128/864 |
| 5,868,682 A | 2/1999 | Combe et al. | |
| 5,944,711 A | 8/1999 | Pender | |
| 6,004,274 A | 12/1999 | Nolan et al. | |
| 6,016,499 A | 1/2000 | Ferguson | |
| 6,024,726 A | 2/2000 | Hill | |
| 6,129,174 A | 10/2000 | Brown et al. | |
| 6,139,507 A | 10/2000 | Jeng | |
| 6,159,171 A | 12/2000 | Densert et al. | |
| 6,186,959 B1 | 2/2001 | Canfield et al. | |
| 6,258,067 B1 | 7/2001 | Hill | |
| 6,359,993 B2 | 3/2002 | Birmhall | |
| 6,430,443 B1 | 8/2002 | Karell | |
| 6,511,437 B1 | 1/2003 | Nakamura et al. | |
| 6,592,512 B2 | 7/2003 | Stöckert et al. | |
| 6,629,938 B1 | 10/2003 | Engvall et al. | |
| 6,725,568 B2 | 4/2004 | Gronka | |
| 6,748,275 B2 | 6/2004 | Lattner et al. | |
| 6,800,062 B2 | 10/2004 | Epley | |
| 6,820,717 B2 | 11/2004 | Fleming et al. | |
| 6,878,128 B2 | 4/2005 | MacMahon et al. | |
| 6,958,043 B2 | 10/2005 | Hissong | |
| 6,981,569 B2 | 1/2006 | Stilp | |
| 7,022,090 B1 | 4/2006 | Engvall et al. | |
| 7,162,039 B1 | 1/2007 | Callahan | |
| 7,179,238 B2 | 2/2007 | Hissong | |
| 7,189,252 B2 | 3/2007 | Krueger | |
| 7,268,466 B2 | 9/2007 | Rasmussen | |
| 7,352,871 B1 | 4/2008 | Mozo | |
| D570,457 S | 6/2008 | Brown | |
| 7,613,519 B2 | 11/2009 | De Ridder | |
| 7,766,858 B2 | 8/2010 | Franz et al. | |
| 7,779,844 B2 | 8/2010 | Purcell et al. | |
| 7,785,346 B2 | 8/2010 | Blumberg | |
| 7,797,042 B2 | 9/2010 | Dietrich et al. | |
| 7,833,282 B2 | 11/2010 | Mandpe | |
| 7,892,180 B2 | 2/2011 | Epley | |
| 7,959,597 B2 | 6/2011 | Baker et al. | |
| 7,988,657 B2 | 8/2011 | Shapiro et al. | |
| 8,020,563 B2 | 9/2011 | Pfanstiehl | |
| 8,047,207 B2 | 11/2011 | Perez et al. | |
| 8,052,693 B2 | 11/2011 | Shahoian | |
| 8,122,892 B2 | 2/2012 | Johnson et al. | |
| 8,142,373 B1 | 3/2012 | Riles | |
| 8,199,919 B2 | 6/2012 | Goldstein et al. | |
| 8,241,224 B2 | 8/2012 | Keefe | |
| 8,249,285 B2 | 8/2012 | Killion et al. | |
| 8,251,925 B2 | 8/2012 | Keady et al. | |
| 8,262,717 B2 * | 9/2012 | Rogers | A61H 39/06 607/112 |
| 8,267,983 B2 | 9/2012 | Rogers et al. | |
| 8,267,984 B2 | 9/2012 | Rogers | |
| 8,328,830 B1 | 12/2012 | Pandit | |
| 8,398,562 B2 | 3/2013 | Keller | |
| 8,414,521 B2 | 4/2013 | Baker et al. | |
| 8,442,632 B2 | 5/2013 | Kullok et al. | |
| 8,460,356 B2 | 6/2013 | Rogers et al. | |
| 8,506,469 B2 | 8/2013 | Dietrich et al. | |
| 8,515,552 B2 | 8/2013 | Englehart | |
| 8,550,206 B2 | 10/2013 | Keady et al. | |
| 8,568,348 B2 * | 10/2013 | Vlodaver | A61F 11/00 604/257 |
| 8,603,152 B2 | 12/2013 | Smith et al. | |
| 8,625,833 B1 | 1/2014 | Armwood | |
| 8,666,502 B2 | 3/2014 | Hartlep et al. | |
| 8,688,239 B2 | 4/2014 | Hartlep et al. | |
| 8,696,724 B2 | 4/2014 | Rogers | |
| 8,858,430 B2 | 10/2014 | Oyadiran et al. | |
| 8,963,914 B2 | 2/2015 | Rawat et al. | |
| 9,039,639 B2 * | 5/2015 | George | H04R 1/42 381/165 |
| 9,168,171 B2 | 10/2015 | Rogers | |
| 9,186,277 B2 * | 11/2015 | George | H04R 1/42 |
| 9,283,111 B2 | 3/2016 | Rogers et al. | |
| 9,526,653 B2 | 12/2016 | Rogers et al. | |
| 9,532,900 B2 | 1/2017 | Smith et al. | |
| 9,579,247 B2 | 2/2017 | Juto et al. | |
| 9,655,772 B2 | 5/2017 | Smith et al. | |
| 9,744,074 B2 | 8/2017 | Rogers | |
| 9,849,026 B2 | 12/2017 | Rogers et al. | |

(56) References Cited

U.S. PATENT DOCUMENTS

| | | |
|---|---|---|
| 2002/0069883 A1 | 6/2002 | Hirchenbain |
| 2003/0195588 A1 | 10/2003 | Fischell et al. |
| 2003/0220536 A1 | 11/2003 | Hissong |
| 2004/0097839 A1 | 5/2004 | Epley |
| 2004/0163882 A1 | 8/2004 | Fleming et al. |
| 2005/0065585 A1 | 3/2005 | Salas |
| 2005/0165460 A1 | 7/2005 | Erfan |
| 2005/0209516 A1 | 9/2005 | Fraden |
| 2006/0100681 A1 | 5/2006 | Salas Carpizo |
| 2006/0197412 A1 | 9/2006 | Rasmussen |
| 2006/0253087 A1 | 11/2006 | Vlodaver et al. |
| 2006/0272650 A1 | 12/2006 | Hoogenakker et al. |
| 2007/0060948 A1 | 3/2007 | Franz et al. |
| 2007/0250119 A1 | 10/2007 | Tyler et al. |
| 2007/0299362 A1 | 12/2007 | Epley et al. |
| 2008/0011308 A1 | 1/2008 | Fleming |
| 2008/0154183 A1 | 6/2008 | Baker et al. |
| 2008/0168775 A1 | 7/2008 | Windheim et al. |
| 2008/0208100 A1 | 8/2008 | Wolff |
| 2008/0212787 A1 | 9/2008 | Goldstein et al. |
| 2008/0220092 A1 | 9/2008 | Dipierro |
| 2008/0249439 A1 | 10/2008 | Tracey et al. |
| 2008/0264464 A1 | 10/2008 | Lee et al. |
| 2009/0012420 A1 | 1/2009 | Keller |
| 2009/0082831 A1 | 3/2009 | Paul et al. |
| 2009/0173353 A1 | 7/2009 | Pursell et al. |
| 2009/0182399 A1 | 7/2009 | Sylvestre |
| 2009/0228103 A1 | 9/2009 | Clayton |
| 2010/0002897 A1 | 1/2010 | Keady |
| 2010/0030131 A1 | 2/2010 | Morriss et al. |
| 2010/0071707 A1* | 3/2010 | Wohl .................. A61F 11/00 128/864 |
| 2010/0071708 A1 | 3/2010 | Lenhardt |
| 2010/0179490 A1 | 7/2010 | Connelly et al. |
| 2010/0198282 A1 | 8/2010 | Rogers |
| 2010/0211142 A1 | 8/2010 | Rogers |
| 2011/0079227 A1 | 4/2011 | Turcot et al. |
| 2011/0097141 A1 | 4/2011 | Brown |
| 2011/0098551 A1 | 4/2011 | Zhang |
| 2011/0130786 A1 | 6/2011 | Clayton et al. |
| 2011/0184341 A1 | 7/2011 | Baker et al. |
| 2011/0224493 A1 | 9/2011 | Oyadiran et al. |
| 2011/0245902 A1 | 10/2011 | Katz |
| 2012/0046607 A1 | 2/2012 | Syk |
| 2012/0265093 A1 | 10/2012 | Allen et al. |
| 2012/0296268 A1 | 11/2012 | Vlodavaer et al. |
| 2012/0302859 A1 | 11/2012 | Keefe |
| 2012/0310077 A1 | 12/2012 | Rogers |
| 2012/0310313 A1 | 12/2012 | Rogers et al. |
| 2013/0123889 A1 | 5/2013 | Katz et al. |
| 2013/0136285 A1 | 5/2013 | Naumann |
| 2013/0152949 A1 | 6/2013 | Simon |
| 2013/0177179 A1 | 7/2013 | Ambrose et al. |
| 2013/0282070 A1 | 10/2013 | Cowan et al. |
| 2013/0303953 A1 | 11/2013 | Lattner |
| 2013/0304103 A1 | 11/2013 | Burres |
| 2013/0310907 A1 | 11/2013 | Rogers et al. |
| 2013/0324932 A1 | 12/2013 | Cogley |
| 2014/0069442 A1 | 3/2014 | Lewis et al. |
| 2014/0088671 A1 | 3/2014 | Rogers et al. |
| 2014/0249608 A1 | 9/2014 | Rogers |
| 2014/0275827 A1 | 9/2014 | Gill et al. |
| 2014/0309718 A1 | 10/2014 | Smith et al. |
| 2015/0005661 A1* | 1/2015 | Trammell .............. A61B 5/128 600/559 |
| 2015/0141879 A1 | 5/2015 | Harper et al. |
| 2015/0320591 A1 | 11/2015 | Smith et al. |
| 2015/0320592 A1 | 11/2015 | Black et al. |
| 2015/0374538 A1* | 12/2015 | Rogers .................. A61F 7/12 607/105 |
| 2016/0058620 A1* | 3/2016 | George .................. H04R 1/42 128/868 |
| 2016/0128897 A1 | 5/2016 | George et al. |
| 2016/0151206 A1 | 6/2016 | George et al. |
| 2016/0346117 A1 | 12/2016 | Rogers et al. |
| 2016/0378945 A1 | 12/2016 | Mian et al. |
| 2017/0105876 A1 | 4/2017 | O'Connell, Sr. et al. |
| 2017/0109988 A1 | 4/2017 | O'Connell, Sr. et al. |
| 2017/0135854 A1 | 5/2017 | Rogers et al. |
| 2017/0235889 A1 | 8/2017 | Main et al. |
| 2018/0000686 A1 | 1/2018 | George et al. |
| 2018/0023558 A1 | 1/2018 | George et al. |

FOREIGN PATENT DOCUMENTS

| | | |
|---|---|---|
| CA | 1222464 | 6/1987 |
| CA | 1241152 | 8/1988 |
| CA | 2003452 | 6/1990 |
| CA | 2275057 | 10/1999 |
| CA | 2 337 076 | 1/2000 |
| CA | 2429560 | 1/2004 |
| CN | 2075517 U | 4/1991 |
| CN | 2418864 | 2/2001 |
| CN | 1308513 A | 8/2001 |
| CN | 2530645 | 1/2003 |
| CN | 2912525 | 6/2007 |
| CN | 201143258 | 11/2008 |
| CN | 201164541 | 12/2008 |
| CN | 101668497 | 3/2010 |
| CN | 201524178 | 7/2010 |
| CN | 201558360 | 8/2010 |
| CN | 201870809 | 6/2011 |
| CN | 202036187 | 11/2011 |
| CN | 202185057 | 4/2012 |
| CN | 102484761 | 5/2012 |
| CN | 102551957 | 7/2012 |
| CN | 202313927 | 7/2012 |
| CN | 102647966 | 8/2012 |
| CN | 202477966 | 10/2012 |
| CN | 202505833 | 10/2012 |
| CN | 102986250 | 3/2013 |
| DE | 102011008802 | 7/2012 |
| EP | 0026247 | 4/1981 |
| EP | 0400900 | 12/1990 |
| EP | 1027863 | 8/2000 |
| EP | 2207366 | 7/2010 |
| EP | 2 990 017 | 3/2016 |
| FR | 2 605 516 A1 | 4/1988 |
| GB | 1432572 | 4/1976 |
| GB | 1522031 | 8/1978 |
| GB | 2054387 | 2/1981 |
| GB | 2185688 | 7/1987 |
| GB | 2343263 | 5/2000 |
| GB | 2479891 | 11/2011 |
| IT | 1214840 | 1/1990 |
| JP | 2006345903 | 12/2006 |
| JP | 2009022699 | 2/2009 |
| JP | 2010233643 | 10/2010 |
| JP | 2010233643 | 12/2010 |
| JP | 2011217986 | 11/2011 |
| JP | 2013068448 | 4/2013 |
| JP | 2013102784 | 5/2013 |
| MX | 9705652 | 7/1998 |
| MX | PA03005598 | 10/2004 |
| MX | 2010014470 | 2/2011 |
| MX | 2011006854 | 8/2011 |
| MX | 2012007726 | 8/2012 |
| WO | 86/01399 | 3/1986 |
| WO | WO 94/22372 | 10/1994 |
| WO | WO 1996/23293 | 8/1996 |
| WO | WO 1997/23178 | 7/1997 |
| WO | 2000/001331 | 1/2000 |
| WO | 2000/001346 | 1/2000 |
| WO | 2000/010484 | 3/2000 |
| WO | WO 00/10627 | 3/2000 |
| WO | WO 2000/010484 | 3/2000 |
| WO | WO 03/075761 | 9/2003 |
| WO | WO 2004/064672 | 8/2004 |
| WO | 2004/100844 | 11/2004 |
| WO | WO 2004/100844 | 11/2004 |
| WO | WO 2006/009545 | 1/2006 |
| WO | WO 2007/084674 | 7/2007 |
| WO | WO 2007/118092 | 10/2007 |
| WO | WO 2007/145853 | 12/2007 |

(56) References Cited

FOREIGN PATENT DOCUMENTS

| | | |
|---|---|---|
| WO | WO 2008/036368 | 3/2008 |
| WO | WO 2008/064230 | 5/2008 |
| WO | WO 2008/086187 | 7/2008 |
| WO | WO 2008/128173 | 10/2008 |
| WO | WO 2008/153588 | 12/2008 |
| WO | WO 2009/020862 | 2/2009 |
| WO | WO 2009/050306 | 4/2009 |
| WO | WO 2009/077902 | 6/2009 |
| WO | WO 2009/077902 | 10/2009 |
| WO | WO 2010/005899 | 1/2010 |
| WO | WO 2010/016925 | 2/2010 |
| WO | WO 2010/085196 | 7/2010 |
| WO | WO 2011/075573 | 6/2011 |
| WO | WO 2011/075574 | 6/2011 |
| WO | 2012/007193 | 1/2012 |
| WO | WO 2012/083098 | 6/2012 |
| WO | WO 2012/083102 | 6/2012 |
| WO | WO 2012/083106 | 6/2012 |
| WO | WO 2012/083126 | 6/2012 |
| WO | WO 2012/083151 | 6/2012 |
| WO | WO 2013/075255 | 5/2013 |
| WO | WO 2014/120947 | 8/2014 |
| WO | WO 2014/210457 | 12/2014 |
| WO | WO 2015/009421 | 1/2015 |
| WO | 2015/074060 | 5/2015 |
| WO | WO 2016/022761 | 2/2016 |
| WO | WO 2017/040739 | 3/2017 |
| WO | WO 2017/040741 | 3/2017 |
| WO | WO 2017/040747 | 3/2017 |
| ZA | 200509787 | 1/2009 |

OTHER PUBLICATIONS

Baguley et al. Does caloric vestibular stimulation modulate tinnitus? Neuroscience Letters, Mar. 2011, 492(1), pp. 52-54.
Baier et al. Vestibular-Evoked Myogenic Potentials in "Vestibular Migraine" and Meniere's Disease. Ann. N.Y. Acad. Sci., May 2009, 1164, pp. 324-327.
Bolay et al. Does Low Atmospheric Pressure Independently Trigger Migraine? Headache, Oct. 2011, 51(9), pp. 1426-1430.
Dirckx et al. Human tympanic membrane deformation under static pressure. Hearing Research, Jan. 1991, 51(1), pp. 93-105.
Fasold et al. Human Vestibular Cortex as Identified with Caloric Stimulation in Functional Magnetic Resonance Imaging. NeuroImage, Nov. 2002, 17(3), pp. 1384-1393.
Job et al. Cortical Representation of Tympanic Membrane Movements due to Pressure Variation: An fMRI Study. Human Brain Mapping, May 2011, 32(5), pp. 744-749.
Klingner et al. Components of vestibular cortical function. Behavioral Brain Research, Jan. 2013, 236(1), pp. 194-199.
McGeoch et al. Vestibular stimulation can relieve central pain of spinal origin. Spinal Cord, Nov. 2008, 46(11), pp. 756-757.
Nagai et al. Encapsulated nerve corpuscles in the human tympanic membrane. Archives of Otorhinolaryngology, 1989, 246(3), pp. 169-172.
Nihashi et al. Representation of the ear in human primary somatosensory cortex. NeuroImage, Feb. 2001, 13(2), pp. 295-304 (abstract only).
Porta-Etessam et al. Neuro-otological symptoms in patients with migraine. Neurologia, Mar. 2011, 26(2), pp. 100-104.
Ramachandran et al. Rapid Relief of Thalamic Pain Syndrome Induced by Vestibular Caloric Stimulation. Neurocase, Jun. 2007, 13(3), pp. 185-188.
Sakata et al. Air pressure-sensing ability of the middle ear—Investigation of sensing regions and appropriate measurement conditions. Auris Nasus Larynx, Aug. 2009, 36(4), pp. 393-399.
Schulman. Breath-Holding, Head Pressure, and Hot Water: An Effective Treatment for Migraine Headache. Headache, Nov.-Dec. 2002, 42(10), pp. 1048-1050.
Breathometer. Breathometer—The World's First Smartphone Breathalyzer. Website, http://www.breathometer.com, originally downloaded Jun. 19, 2014, 8 total pages.
U.S. Appl. No. 61/841,111, filed Jun. 28, 2013.
Scion Neurostim. Therapeutic Neuromodulation via Caloric Vestibular Stimulation. Thermoneuromodulation (TNM). Slides for presentation, dated Sep. 2015, 12 pages total.
Cadwell. Sierra Wave. Website, http://www.cadwell.com, originally downloaded Feb. 27, 2014, 1page.
Ferrotec. Thermal Solutions. Website, https://thermal.ferrotec.com, originally downloaded Feb. 27, 2014, 1page.
Ferrotec. Thermoelectric Technical Reference—Installation of Thermoelectric Modules. Website, https://thermal.ferrotec.com, originally downloaded May 21, 2014, 4 total pages.
Ferrotec. Thermoelectric Technical Reference—Introduction to Thermoelectric Cooling. Website, https://www.ferrotec.com, originally downloaded Feb. 27, 2014, 2total pages.
Kolev. How caloric vestibular irrigation influences migraine attacks. Cephalalgia. Aug. 1990, vol. 10, Issue 4, pp. 167-169 (abstract only).
Lifting the Burden. The Global Campaign Against Headache. Website, http://www.l-t-b.org, originally downloaded Feb. 27, 2014, 1 page.
Long Island News12.com. Long Island Naturally: Migraines. Website video, http://longisland.news12.com/multimedia/long-island-naturally-migraines-1.6501113, Nov. 26, 2013, 3 total.
Medscape. Peripheral Nerve Stimulator—Train of Four Monitoring. Website, http://emedicine.medscape.com, originally downloaded Feb. 27, 2014, 2 total pages.
Medtronic. Meniett Device for Meniere's Disease. Meniett Low-Pressure Pulse Generator device. Website, http://www.medtronic.com, originally downloaded Feb. 27, 2014, 2 total page.
New York Health Solutions. Migraine Headaches. Website, http://www.nyhealthsolutions.com, originally downloaded May 23, 2014, 2 total pages.
Pietrobon. Migraine: new molecular mechanisms. Neuroscientist. Aug. 2005, vol. 11, Issue 4, pp. 373-386 (abstract only).
Saunders. Tympanic membrane sensation. Brain. Jun. 1985, vol. 108, Issue 6, pp. 387-404 (abstract only).
Sheftell, F, Steiner, TJ, Thomas, H. Harry Potter and the Curse of Headache. Headache: The Journal of Head and Face Pain. Jun. 2007, vol. 47, Issue 6, pp. 911-916 (abstract only).
Smartproducts. Series 100—Cartridge Specialty Check Valves and Pressure Relief Valves. Online catalog, www.smartproducts.coom, originally downloaded Mar. 28, 2014, 2 total pages.
Stovner, LJ, et al. The global burden of headache: a documentation of headache prevalence and disability worldwide. Cephalalgia, 2007. vol. 27, pp. 193-210.
Sullivan. Ear Insufflation as a Novel Therapy Which Produces Rapid Relief of Migraine Headache. Funct Neurol Rehabil Egon 2013; vol. 3, Issue 1, pp. 93-107.
Sullivan. Ear Insufflation Produces Rapid and Significant Relief of Trigeminal Neuraliga. Funct Neurol Rehabil Egon 2013; vol. 3, Issue 4, pp. 1-6.
Ultimate Ears. Ultimate Ears Custom In-Ear Monitors. Website, http://pro.ultimateears.com, originally downloaded Feb. 27, 2014, 3 total pages.
Westone. Occupational Earpieces. Website, http://www.westone.com, originally downloaded Feb. 27, 2014, 2 total pages.
Wikipedia. Microcurrent electrical neuromuscular stimulator. Website, http://en.wikipedia.org, originally downloaded Feb. 27, 2014, 3 total pages.
Wikipedia. Somatosensory evoked potential. Website, http://en.wikipedia.org, originally downloaded Feb. 27, 2014, 5 total pages.
Wikipedia. Transcutaneous electrical nerve stimulation. Website, http://en.wikipedia.org, originally downloaded Feb. 27, 2014, 5 total pages.
World Health Organization. Headache disorders. Website, http://www.who.int, originally downloaded Feb. 27, 2014, 4 total pages.
U.S. Appl. No. 61/983,865, filed Apr. 24, 2014.
U.S. Appl. No. 61/863,317, filed Aug. 7, 2013.
Akerman, et al. Pearls and pitfalls in experimental invivo models of migraine: Dural trigeminovascular nociception. Cephalagia, 2013, 33 (8), pp. 557-592.

(56) References Cited

OTHER PUBLICATIONS

Dasilva et al. tdCS-Induced Analgesia and Electrical Fields in Pain-Related Neural Networks in Chronic Migraine. The Journal of Head and Face Pain, Sep. 2012, 52, pp. 1283-1295.
Hu et al. Burden of migraine in the United States: disability and economic costs. Arch. Intern. Med., Apr. 1999, 159, pp. 813-818.
Janetta Neurovascular Compress in Cranial Nerve and Systemic Disease. Ann Surg, Oct. 1980, 192(4), pp. 518-524.
Meng et al. Migraine Prevention with a Supraorbital Transcutaneous Stimulator: A Randomized Controlled Trial. Neurology, Sep. 2013, 81, pp. 1102-1103.
Mosqueria et al. Vagus Nerve Stimulation in Patients with Migraine. Rev Neurol, 2013, 57(2), English Abstract.
Olesen et al. Emerging Migraine treatments and drug targets. Trends in Pharmacological Sciences, 2011, 32(6), pp. 352-359.
Pederson et al. Neurostimulation in cluster headache: A review of current progress. Cephalagia, 2013, 33(14), pp. 1179-1193.
Schoenen et al. Migraine prevention with a supraorbital transcutaneous stimulator. Neurology, 2013, 80(8), pp. 697-704.
Silberstein et al. Botulinum Toxin Type A as a Migraine Preventive Treatment. The Journal of Head and Face Pain, Jun. 2000, 40, pp. 445-450.
New Zealand Patent Application No. 713887; Office Action dated Jul. 13, 2016, 8 pages total.
Sameiro-Barbosa et al. Sensory Entrainment Mechanisms in Auditory Perception: Neural Synchronization Cortico-Striatal Activation. Frontiers in Neuroscience, Aug. 2016, vol. 10, Article 361, 8 pages.
Pasadena Pain Masnagement. Easing Migraine Symptoms with a Simple Puff of Air into the Ear; article by Dr. Stender. Website, http://www.pasadenapainmanagment.com, originally downloaded Apr. 25, 2016, 5 pages total.
Smile Columbia Dentistry. Let Me Blow in Your Ear, for Migraine Treatment, of Course; article by Dr. Adam Hahn. Website, https://www.tmjtreatmentse.com, originally downloaded Apr. 25, 2016, 2 pages total.
U.S. Appl. No. 07/286,744, filed Dec. 19, 1988.
Facebook. ZōK: The first migraine and headache solution. Webpage, https://www.facebook.com, originally downloaded May 18, 2017, 10 pages total.
Kickstarter. ZōK: The first headache product that solves migraines and headaches. Website, https:www.funded.today, originally downloaded May 18, 2017, 3 pages total.
Chinese Patent Application No. 201480042665.7; Office Action dated Jan. 22, 2017, 26 pages total.
New Zealand Patent Application No. 713887; Office Action dated Feb. 20, 2017, 9 pages total.
Sullivan: "Ear Insufflation as a Novel Therapy Which Produces Rapid Relief of Migraine Headache—a Case Study," Funct Neurol Rehabil Egon 2013; vol. 3, Issue 1, pp. 93-107. Published on Jun. 7, 2013. Received on Jan. 2, 2013. Revised Jan. 28, 2013. Accepted Feb. 15, 2013.
Sullivan: "Ear Insufflation Produces Rapid and Significant Relief of Trigeminal Neuraliga," Funct Neurol Rehabil Egon 2013; vol. 3, Issue 4, pp. 1-6. Published on May 26, 2014. Received on Jun. 21, 2013. Revised Dec. 24, 2013. Accepted Jan. 12, 2014.
Becker: Weather and migraine: Can so many patients be wrong? Cephalalgia, Mar. 2011, 31(4), pp. 387-390.
George et al. Safety and usability factors in development of a novel, automated treatment device for acute migraine. Biomedical sciences instrumentation. Biomedical sciences instrumentation, Jan. 2017, 53, pp. 398-403.
Liszewski: Ear Pressure Equalizer. Website, http://www.ohgizmo.com, originally downloaded Dec. 18, 2013, 1 page.
Mayr: The Origins of Feedback Control. M.I.T. Press, 1970.
Medtronic. Restore Life's Balance with Meniett Therapy. The Meniett Device for Meniere's Disease. On-line article, http://www.medtronic.com, originally downloaded Mar. 13, 2015, 2 total pages.
Minen. Tinnitus and Headache. American Migraine Foundation, website, downloaded Feb. 8, 2017, 3 pages total.
U.S. Appl. No. 61/905,616, filed Nov. 18, 2013.
Patent Cooperation Treaty International Patent Application No. PCT/US2014/0066191; Written Opinion of the International Searching Authority dated Feb. 26, 2015, 7 pages total.

\* cited by examiner

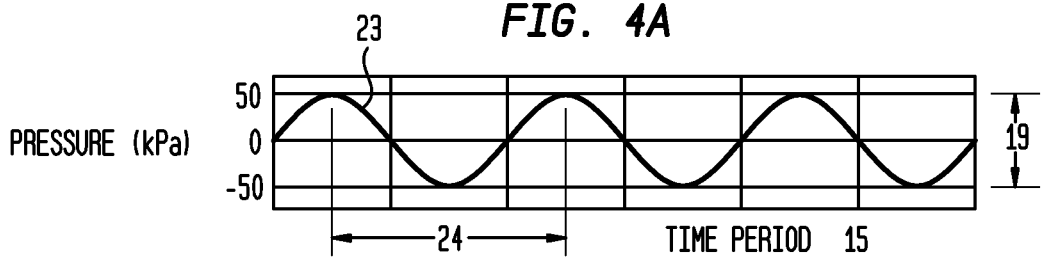
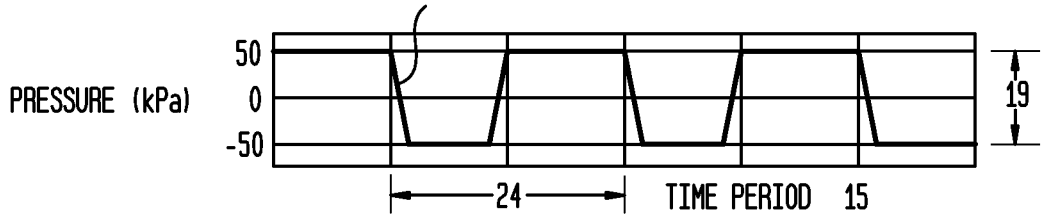
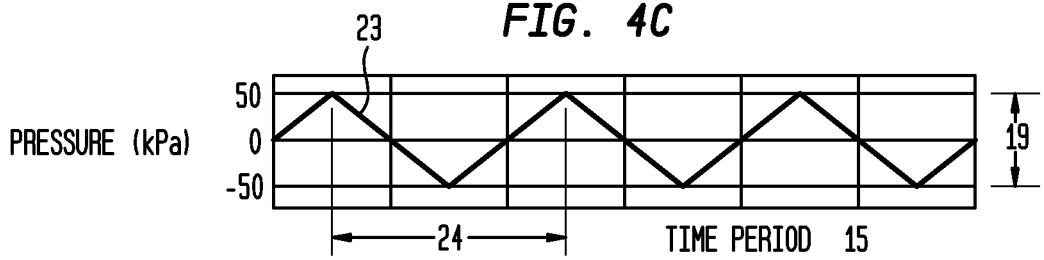
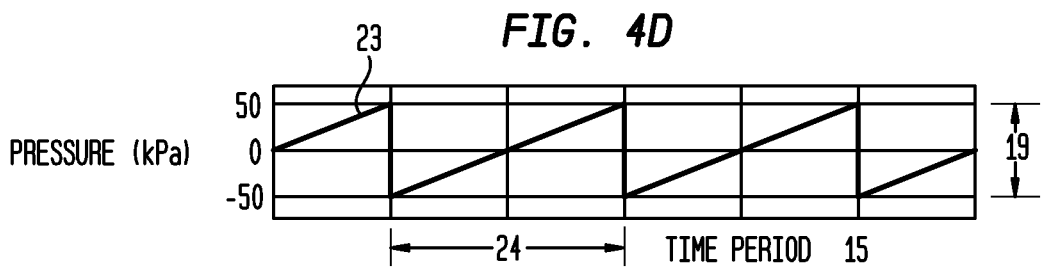
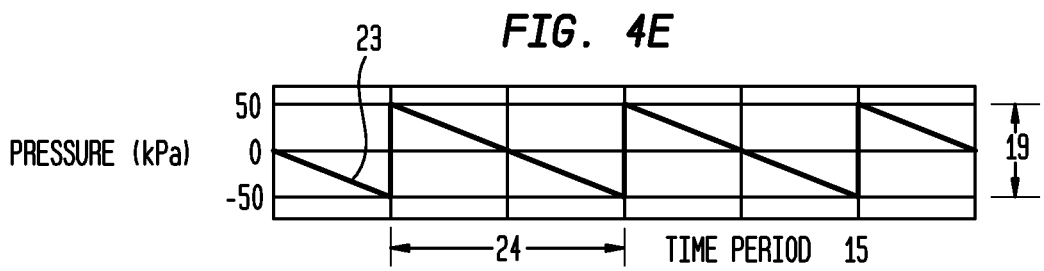

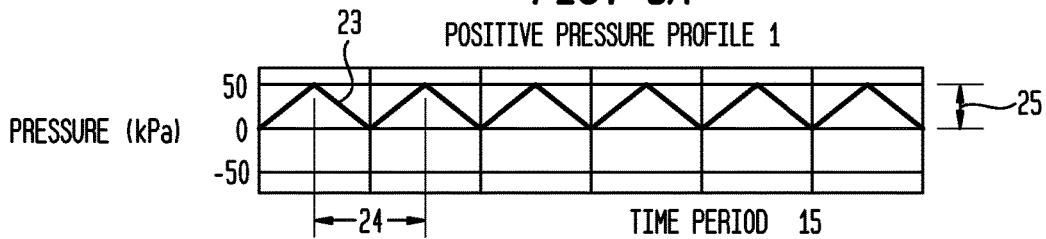
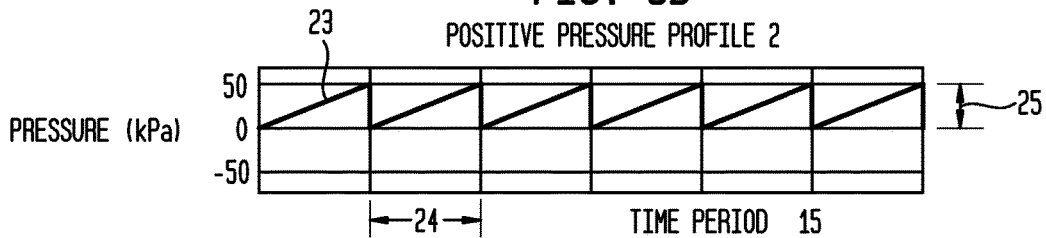
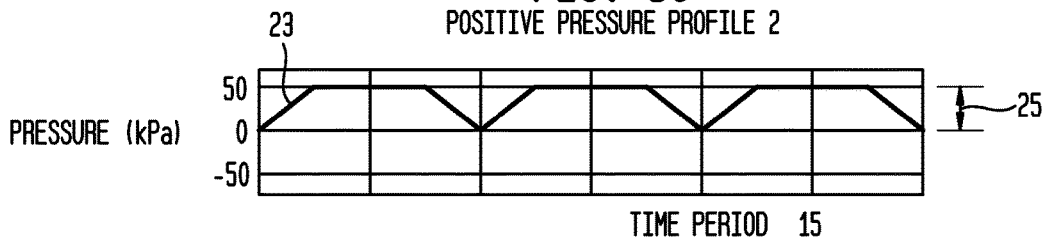
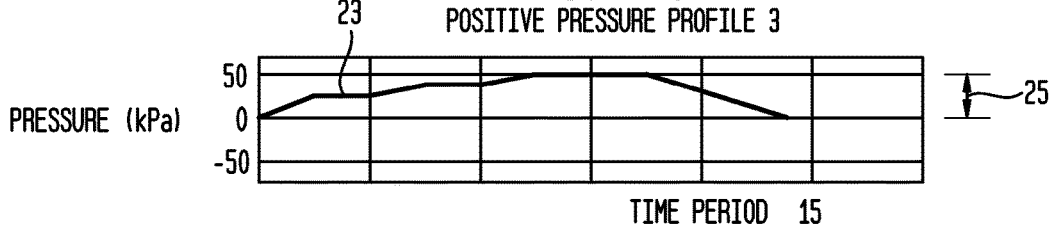
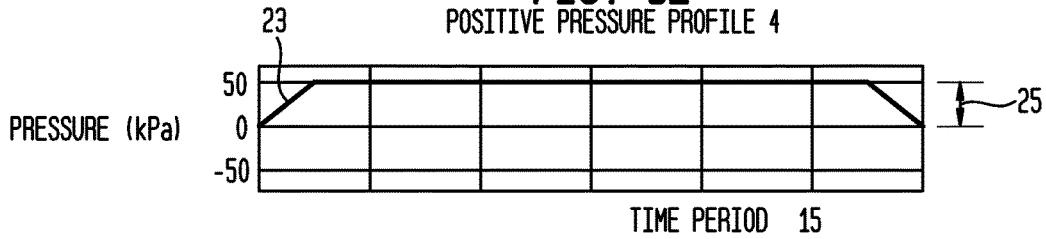

METHOD FOR EXTERNAL EAR CANAL PRESSURE REGULATION TO ALLEVIATE DISORDER SYMPTOMS

This U.S. Non-Provisional patent application claims the benefit of U.S. Provisional Patent Application No. 61/983,865, filed Apr. 24, 2014, U.S. Provisional Patent Application No. 61/863,317, filed Aug. 7, 2013, and U.S. Provisional Patent Application No. 61/841,111, filed Jun. 28, 2013, each hereby incorporated by reference herein.

I. BACKGROUND OF THE INVENTION

Neurologically-mediated pain or discomfort associated with a disorder, such as craniofacial pain syndromes or headache syndromes, may negatively impact the quality of life of the sufferer. In addition to the burden upon the individual, chronic neurological conditions may be a significant strain upon family members, employers, and the healthcare system.

Regarding migraine headaches, concomitant symptoms such as pain, nausea, aura, photophobia, dysesthesias, dizziness, vertigo, and dysequilibrium may represent a significant burden to the population. Epidemiological studies indicate that, in the United States, approximately 18% of women and 6% of men experience frequent migraine headaches and 2% of the general population suffer from chronic migraine headaches. Additionally, persons suffering with chronic migraine headaches or other headaches of similar severity and disability may be at a significantly greater risk for depression and attempted suicide. Thus, it is prudent for clinicians and researchers to continue searching for effective therapies and methodologies to alleviate the symptoms associated with these disorders or treat the disorders.

Standard pharmaceutical therapies for migraine headaches may generally be prescribed to prevent pain or to relieve pain. The various agents which fall under these two broad categories may exhibit a wide range of effectiveness and also incur varying degrees of side effects. From the perspective of economics, the expense of these medications may be a major source of financial burden on the consumer. Moreover, advanced interventions such as botulinum toxin injections, nerve blockades, neurosurgical alterations, and implanted electrical stimulators may significantly increase costs associated with treatment, while subjecting patients to potential changes in their anatomy and physiology, with no guarantee of complete or permanent symptomatic relief or disorder resolution. Furthermore, one of the most widely used abortive agent categories in current migraine treatment may not be appropriate for those with cardiovascular risk factors, which may pose a significant population considering the prevalence of cardiovascular disease.

There is a burgeoning field of understanding and applications within the neurosciences which seek to affect positive physiological changes in the nervous system through non-pharmaceutical and non-surgical applications. This field of 'functional neurology' views the human nervous system as a receptor driven system, which may be activated and stimulated in specific ways to produce adaptive, long-term changes through the process of neuroplasticity. This approach to neurorehabilitation utilizes, but not necessarily exclusively, various forms and patterns of receptor activation or deactivation to promote positive neurophysiological adaptations within the central nervous system, including the brain, brainstem, and spinal cord, which may promote optimized physiological function of associated tissues, organs, and systems.

There would be a substantial advantage in providing a method which can achieve beneficial targeted central nervous system excitation through various stimuli via cranial nerves and concomitant brainstem integration. Particularly, there would be a substantial advantage in providing an effective non-pharmaceutical and non-surgical method having a low side-effect profile for the alleviation of neurologically-mediated pain or discomfort associated with a disorder, such as craniofacial pain syndromes or headache syndromes, or for the treatment of the disorder.

II. SUMMARY OF THE INVENTION

A broad object of particular embodiments of the invention can be to provide a method for external ear canal pressure regulation to alleviate one or more symptoms associated with a disorder or treat one or more disorders.

Another broad object of particular embodiments of the invention can be to provide a method for external ear canal pressure regulation to alleviate a disorder symptom or treat a disorder, the method including obtaining a fluid transfer device which generates a fluid flow of a fluid through an earplug, the earplug having an earplug external surface configured to sealably engage an external ear canal wall as a barrier between an external ear canal pressure and an ambient pressure; sealably engaging the earplug of the fluid transfer device with the external ear canal wall as the barrier between the external ear canal pressure and the ambient pressure; and operating the fluid transfer device to generate the fluid flow of the fluid through the earplug to achieve an external ear canal pressure differential between the external ear canal pressure and the ambient pressure effective to alleviate a disorder symptom or treat a disorder.

Another broad object of particular embodiments of the invention can be to provide a method for external ear canal pressure regulation to alleviate a disorder symptom or treat a disorder, the method further including flowing a fluid volume within the external ear canal in accordance with one or a combination of pressure regulation profiles.

Another broad object of particular embodiments of the invention can be to provide a method for external ear canal pressure regulation to alleviate a disorder symptom or treat a disorder, the method further including a combination of adjusting a temperature of the fluid to a fluid temperature lesser than or greater than a body temperature.

Naturally, further objects of the invention are disclosed throughout other areas of the specification, drawings, and claims.

III. BRIEF DESCRIPTION OF THE DRAWINGS

FIG. 4A is a graph of a pressure regulation profile useful in a particular embodiment of the inventive method.

FIG. 4B is a graph of a pressure regulation profile useful in a particular embodiment of the inventive method.

FIG. 4C is a graph of a pressure regulation profile useful in a particular embodiment of the inventive method.

FIG. 4D is a graph of a pressure regulation profile useful in a particular embodiment of the inventive method.

FIG. 4E is a graph of a pressure regulation profile useful in a particular embodiment of the inventive method.

FIG. 5A is a graph of a positive pressure regulation profile useful in a particular embodiment of the inventive method.

FIG. 5B is a graph of a positive pressure regulation profile useful in a particular embodiment of the inventive method.

FIG. 5C is a graph of a positive pressure regulation profile useful in a particular embodiment of the inventive method.

FIG. 5D is a graph of a positive pressure regulation profile useful in a particular embodiment of the inventive method.

FIG. 5E is a graph of a positive pressure regulation profile useful in a particular embodiment of the inventive method.

IV. DETAILED DESCRIPTION OF THE INVENTION

Figure 1A:
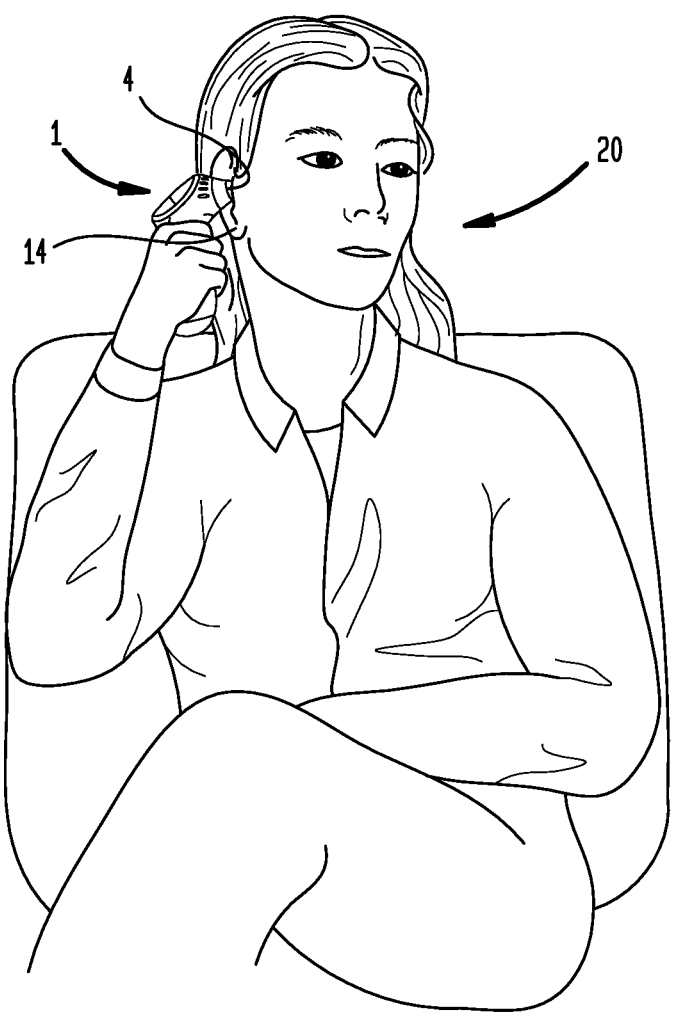
FIG. 1A is an illustration of a method of using a particular embodiment of the inventive method.
Figure 1B:
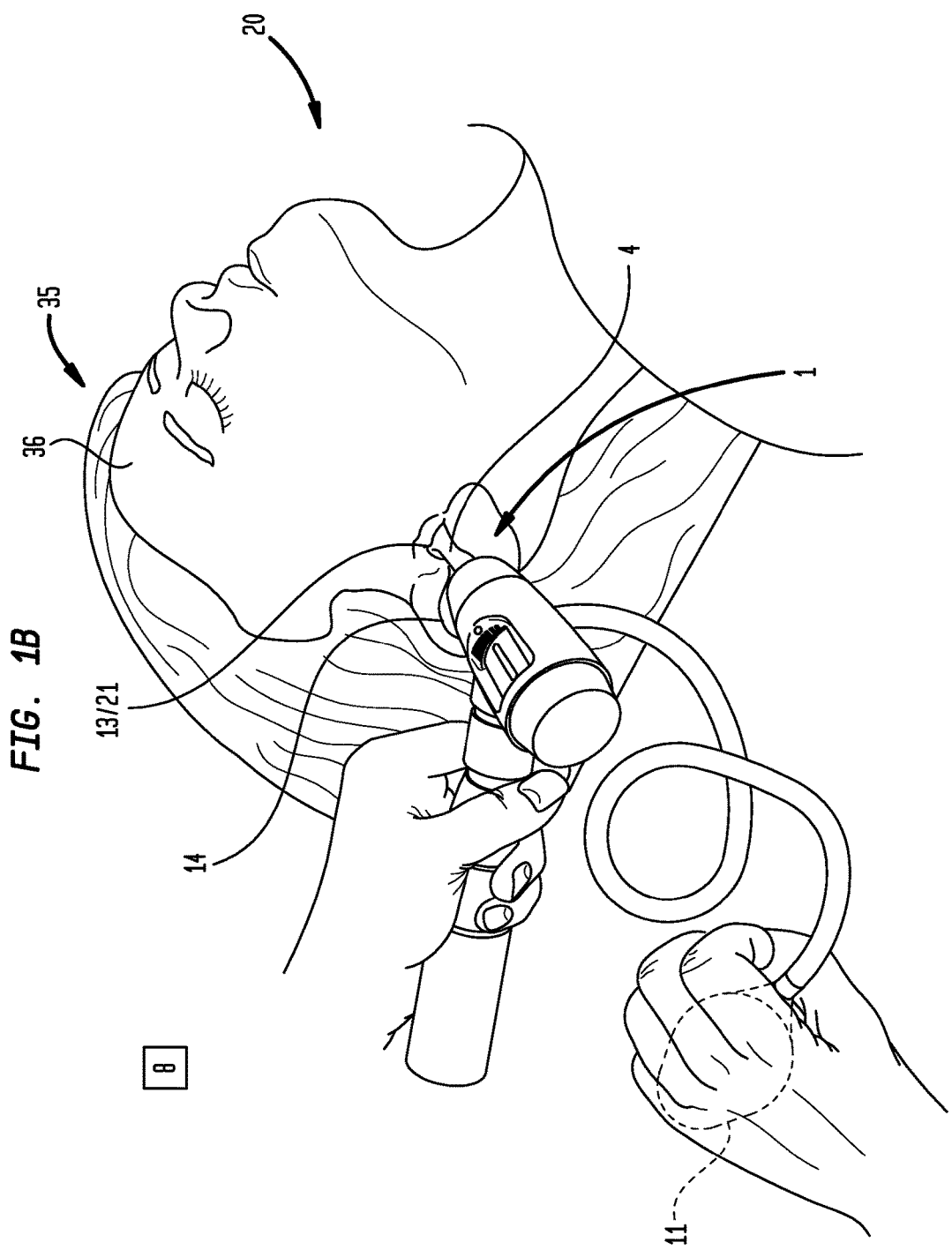
FIG. 1B is an illustration of a method of using a particular embodiment of the inventive method.

Now referring primarily to FIG. 1A and FIG. 1B, which illustrate a method for external ear canal pressure regulation effective to alleviate one or more disorder symptoms, for example neurologically-mediated pain, or treat one or more disorders, for example craniofacial pain syndromes or headache syndromes. The inventive method can include providing a fluid transfer device (1) which generates a fluid flow (2) of a fluid (3) through an earplug (4), the earplug (4) having an earplug external surface (5) configured to sealably engage an external ear canal wall (6) as a barrier between an external ear canal pressure (7) and an ambient pressure (8); sealably engaging the earplug (4) of the fluid transfer device (1) with the external ear canal wall (6) as the barrier between the external ear canal pressure (7) and the ambient pressure (8); and operating the fluid transfer device (1) to generate the fluid flow (2) of the fluid (3) through the earplug (4) to achieve an external ear canal pressure differential (9) between the external ear canal pressure (7) and the ambient pressure (8) effective to alleviate a disorder symptom or treat a disorder.

Figure 2:
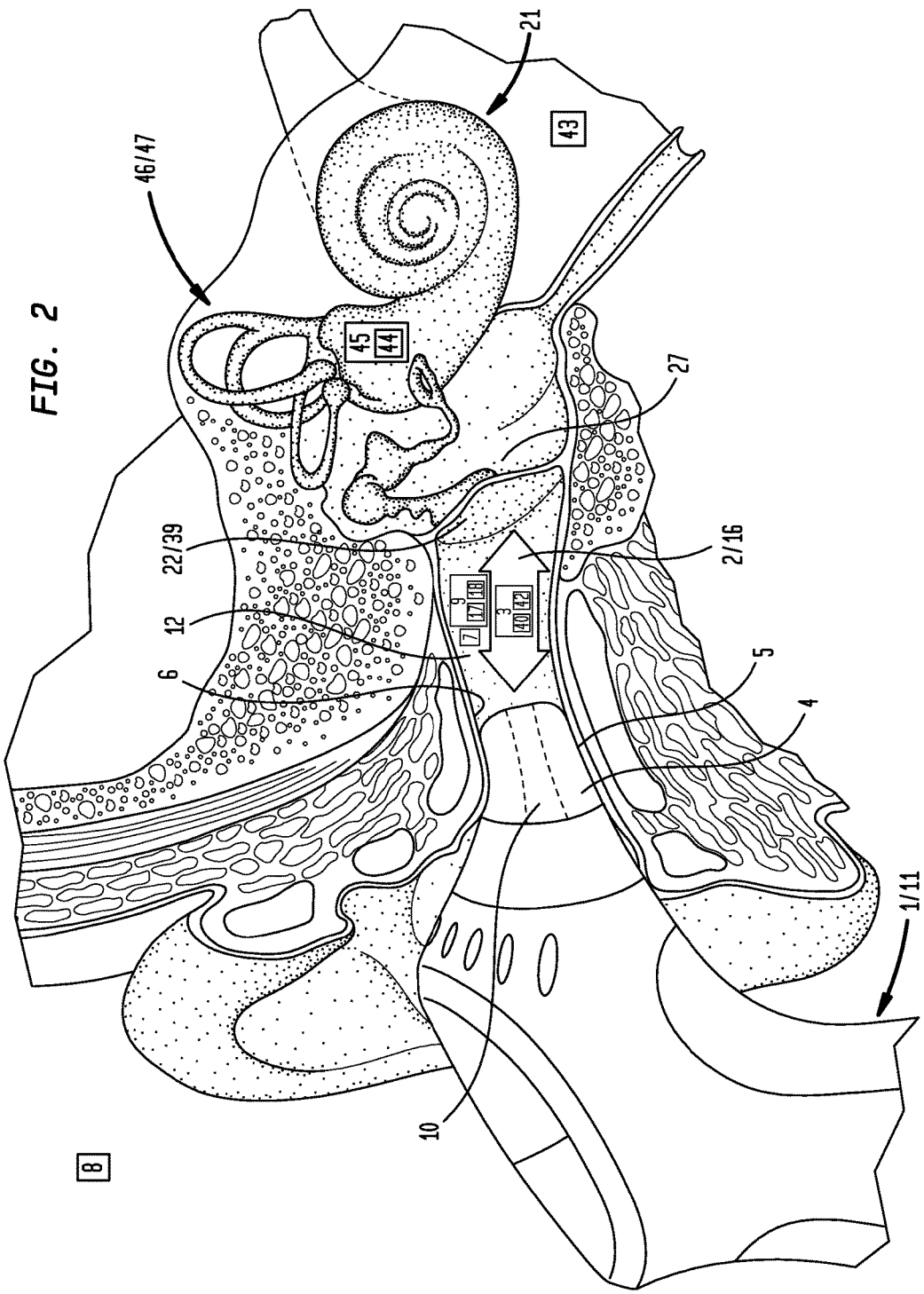
FIG. 2 is an illustration of a method of using a particular embodiment of the inventive method.

Now referring primarily to FIG. 1A through FIG. 2, embodiments of the fluid transfer device (1) can include an earplug (4) having a fluid flow passage (10) fluidicly coupled to a fluid flow generator (11). The earplug external surface (5) capable of sealable engagement with the external ear canal wall (6) can be inserted into the external ear canal (12) of the external auditory meatus (13) of the ear (14). The earplug (4) sealably engaged with the external ear canal wall (6) can function as a barrier between the external ear canal pressure (7) and the ambient pressure (8), allowing regulation or maintenance of an external ear canal pressure differential (9) over a time period (15) during application of the method. The fluid transfer device (1) disposed in relation to the ear (14) as described above can be operated by manipulating the fluid flow generator (11) to generate a fluid flow (2) of a fluid (3) between the fluid flow generator (11) and the external ear canal (12) through the fluid flow passage (10) of the earplug (4) to achieve an external ear canal pressure differential (9) between the external ear canal pressure (7) and the ambient pressure (8). The external ear canal pressure differential (9) can be effective to alleviate a disorder symptom or treat a disorder.

However, the description and figures of the fluid transfer device (1) included herein are not intended to be limiting with respect to the numerous configurations of devices which can be used for generating a fluid flow (2) of a fluid (3) through an earplug (4) to achieve an external ear canal pressure differential (9) between the external ear canal pressure (7) and the ambient pressure (8) in accordance with embodiments of the inventive method for alleviating a disorder symptom or treating a disorder. Rather, the description of the fluid transfer device (1) along with the figures is intended to provide a person of ordinary skill in the art a description sufficient to make and use a wide variety of fluid transfer devices (1) for generating a fluid flow (2) of a fluid (3) through an earplug (4) to achieve an external ear canal pressure differential (9) between the external ear canal pressure (7) and the ambient pressure (8) to alleviate a disorder symptom or treat a disorder.

Additionally, while the fluid transfer device (1) above described delivers a flow of air (16) to the external ear canal (12) to achieve an external ear canal pressure differential (9) between the external ear canal pressure (7) and the ambient pressure (8), this is not intended to be limiting with respect to the wide variety of fluids (3) which can be delivered to the external ear canal (12) to achieve an external ear canal pressure differential (9) between the external ear canal pressure (7) and the ambient pressure (8) to alleviate a disorder symptom or treat a disorder. As an illustrative example, the wide variety of fluids (3) can include: a purified gas, such as oxygen, nitrogen, argon, or the like; a mixture of partial pressures of gases; a liquid, such as water, oil, alcohol, or the like; or combinations thereof. The fluid can also include other compositions or solutions for cleaning, lubricating, disinfecting, or the like, or combinations thereof, and can, for example, include carbamide peroxide, sodium bicarbonate, glycerine, *arachis* oil, turpentine, dichlorobenzene triethanolamine, polypeptides, oleate-condensate, urea hydrogen peroxide, detergent, or the like, or combinations thereof.

A symptom of a disorder can be alleviated by achieving an external ear canal pressure differential (9) between the external ear canal pressure (7) and the ambient pressure (8). The term "symptom" for the purposes of this invention means any discomfort or combination of discomforts associated with a disorder. Without limiting the breadth of the forgoing, symptoms can include: dizziness; vertigo; nausea; imbalance; paresthesia; dysesthesia; sensitivity to light; sensitivity to odor; sensitivity to sound; anxiety; sleeplessness; irritability; fatigue; loss of appetite; blurred vision; gut disturbances; acute pain or chronic pain of varying characteristics including but not limited to throbbing, tearing, sharp, dull, deep, lancinating, burning, aching, stabbing, intense, lightning-like, sense of swelling, or tingling; or the like; or combinations thereof.

The term "disorder" for the purposes of this invention means a physical or mental condition which may not be normal or healthy. Without limiting the breadth of the forgoing, a disorder having one or more associated symptoms which can be alleviated by the inventive method or a disorder which can be treated by the inventive method can include: neuropathic craniofacial pain syndromes such as neuralgias, for example trigeminal neuralgia; temporomandibular joint syndrome; headache syndromes such as migraine headaches, chronic daily headaches, cluster headaches, muscle tension headaches, post-traumatic headaches, or chronic paroxysmal hemicranias; endolymphatic hydrops; vertigo; tinnitus; syndromes resulting from brain injury; syndromes resulting from impaired neurologic function, including cognitive disorders such as attention deficit disorder, emotional disorders such as anxiety disorders, or seizure disorders; phantom limb; middle ear disorders; inner ear disorders; or the like, or combinations thereof.

The term "external ear canal pressure" for the purposes of this invention means forces exerted within the external ear canal (12) and without limitation to the breadth of the forgoing means forces exerted within the external ear canal (12) by a volume of fluid (3), a predetermined volume of fluid (3), or a fluid flow (2) delivered to or generated in to the external ear canal (12) by operation of a fluid transfer device (1).

The term "ambient pressure" for the purposes of this invention means forces exerted external to the external ear canal (12) and without limitation to the breadth of the forgoing means forces exerted on the earplug (4) having the earplug external surface (5) sealably engaged with the external ear canal wall (6), as herein described.

The term "adjustment of pressure" or "adjusting pressure" for the purpose of this invention means to alter the pressure within the external ear canal (12) effective to alleviate a disorder symptom or treat a disorder, which without limiting the breadth of the forgoing, includes achieving a lesser or greater external ear canal pressure (7) in relation to the ambient pressure (8), achieving a lesser or greater ear canal pressure (7) in relation to the ambient pressure (8) over a time period (15), decreasing or increasing the external ear canal pressure (7) in relation to the ambient pressure (8) over a time period (15), whether the decrease or increase is at a constant rate, a variable rate, an incremental rate, or pulsatile within a range of pressures, or combinations thereof.

As to particular embodiments, the inventive method can further include adjusting the external ear canal pressure differential (9) to alleviate one or more disorder symptoms or treat one or more disorders. The external ear canal pressure differential (9) can include a positive external ear canal pressure differential (17) or a negative external ear canal pressure differential (18). As an illustrative example, a positive external ear canal pressure differential (17) can be generated when the fluid transfer device (1) generates a fluid flow (2) of fluid (3) through the fluid flow passage (10) of the earplug (4) to increase the external ear canal pressure (7) relative to the ambient pressure (8). Alternatively, a negative external ear canal pressure differential (18) can be generated when the fluid transfer device (1) generates a fluid flow (2) through the fluid flow passage (10) of the earplug (4) to decrease the external ear canal pressure (7) relative to the ambient pressure (8).

The external ear canal pressure differential (9) can, but not necessarily, have a pressure amplitude (19) in a range of between 0 kilopascals to about 50 kilopascals, whether positive or negative; however, embodiments can have a lesser or greater pressure amplitude (19) depending upon the application. As to particular embodiments, one or more pressure amplitudes (19) useful for the inventive method can be selected from the group including or consisting of: between 0 kilopascals to about 5 kilopascals, between about 2.5 kilopascals to about 7.5 kilopascals, between about 5 kilopascals to about 10 kilopascals, between about 7.5 kilopascals to about 12.5 kilopascals, between about 10 kilopascals to about 15 kilopascals, between about 12.5 kilopascals to about 17.5 kilopascals, between about 15 kilopascals to about 20 kilopascals, between about 17.5 kilopascals to about 22.5 kilopascals, between about 20 kilopascals to about 25 kilopascals, between about 22.5 kilopascals to about 27.5 kilopascals, between about 25 kilopascals to about 30 kilopascals, between about 27.5 kilopascals to about 32.5 kilopascals, between about 30 kilopascals to about 35 kilopascals, between about 32.5 kilopascals to about 37.5 kilopascals, between about 35 kilopascals to about 40 kilopascals, between about 37.5 kilopascals to about 42.5 kilopascals, between about 40 kilopascals to about 45 kilopascals, between about 42.5 kilopascals to about 47.5 kilopascals, and between about 45 kilopascals to about 50 kilopascals. The one or more pressure amplitudes (19) desired for use in particular embodiments of the inventive method can be influenced by such factors as auditory meatus anatomy, physiology, or biochemistry; disorder symptom targeted for alleviation; disorder targeted for treatment; observable effect(s) of the inventive method; or the like; or combinations thereof; but not so much as to cause discomfort to a user (20) or injury to an auditory meatus (21) or a tympanic membrane (22).

Particular embodiments of the inventive method can further include maintaining a constant pressure amplitude (19) over a time period (15) to alleviate a disorder symptom or treat a disorder. As to particular embodiments, a constant pressure amplitude (19) can be maintained substantially without fluid flow (2) of a fluid (3) within the external ear canal (12) over the time period (15). As an illustrative example, the fluid transfer device (1) having the earplug (4) disposed in relation to the ear (14), as described above, can be operated by manipulating the fluid flow generator (11) to generate a fluid flow (2) of a fluid (3) between the fluid flow generator (11) and the external ear canal (12) through the fluid flow passage (10) of the earplug (4) to achieve an external ear canal pressure differential (9) between the external ear canal pressure (7) and the ambient pressure (8). Once the desired external ear canal pressure differential (9) has been achieved, the pressure amplitude (19) can be maintained for a time period (15) without additional fluid flow (2) of the fluid (3), for example by sealably engaging the earplug external surface (5) with the external ear canal wall (6) to achieve a substantially leak-tight or leak-tight barrier along with operation of a valve configured to allow unidirectional fluid flow (2) of the fluid (3) through the fluid flow passage (10) such that the fluid (3) can only either ingress or egress from the external ear canal (12). As to other embodiments, once the desired external ear canal pressure differential (9) has been achieved, the pressure amplitude (19) can be maintained for a time period (15) by additional fluid flow (2) of a fluid (3) to or from the external ear canal (12) to offset leakage about engagement of the earplug external surface (5) and the external ear canal wall (6). As to other embodiments, the pressure amplitude (19) can be maintained for a time period (15) by continuous fluid flow (2) of a fluid (3) in the external ear canal (12).

The constant pressure amplitude (19) can be maintained over a time period (15) to alleviate a disorder symptom or treat a disorder, whereby the constant pressure amplitude (19) can be in a range of between about −50 kilopascals to about +50 kilopascals. A positive external ear canal pressure differential (17) can be achieved by maintaining the constant pressure amplitude (19) in a range of between about 0 kilopascals to about +50 kilopascals. Alternatively, a negative external ear canal pressure differential (18) can be achieved by maintaining the constant pressure amplitude (19) in a range of between about −50 kilopascals to about 0 kilopascals.

Particular embodiments of the inventive method can further include oscillating the pressure amplitude (19) to generate a pressure wave (23) having a pressure wave frequency (24) which can drive a reciprocal fluid flow (2) of a fluid (3) in the external ear canal (12) over a time period (15) to alleviate a disorder symptom or treat a disorder (as shown in the example of FIG. 4A through FIG. 6D). The pressure wave (23) can typically have a pressure wave frequency (24) in a range of between 0 Hertz to about 10 Hertz; however, embodiments can have a lesser or greater pressure wave frequency (24) depending upon the application. As to particular embodiments, one or more pressure wave frequencies (24) can be selected from the group including or consisting of: between 0 Hertz to about 1 Hertz, between about 0.5 Hertz to about 1.5 Hertz, between about 1 Hertz to about 2 Hertz, between about 1.5 Hertz to about 2.5 Hertz, between about 2 Hertz to about 3 Hertz, between about 2.5 Hertz to about 3.5 Hertz, between about 3 Hertz to about 4 Hertz, between about 3.5 Hertz to about 4.5 Hertz, between about 4 Hertz to about 5 Hertz, between about 4.5 Hertz to about 5.5 Hertz, between about 5 Hertz to about 6 Hertz, between about 5.5 Hertz to about 6.5 Hertz, between about 6 Hertz to about 7 Hertz, between about 6.5 Hertz to about 7.5 Hertz, between about 7 Hertz to about 8 Hertz, between about 7.5 Hertz to about 8.5 Hertz, between about 8 Hertz to about 9 Hertz, between about 8.5 Hertz to about 9.5 Hertz, and between about 9 Hertz to about 10 Hertz. The one or more pressure wave frequencies (24) desired for use in particular embodiments of the inventive method can be influenced by such factors as auditory meatus anatomy, physiology, or biochemistry; disorder symptom targeted for alleviation; disorder targeted for treatment; observable effect(s) of the inventive method; or the like; or combinations thereof; but not so much as to cause discomfort to a user (20) or injury to the auditory meatus (21) or the tympanic membrane (22).

As to particular embodiments of the inventive method which include oscillating the pressure amplitude (19) to generate a pressure wave (23) having a pressure wave frequency (24) which can drive a reciprocal fluid flow (2) of a fluid (3) in the external ear canal (12), the pressure wave (23) can have a pressure amplitude (19) in a range of between about −50 kilopascals to about +50 kilopascals to alleviate a disorder symptom or treat a disorder.

Now referring primarily to FIG. 4A through FIG. 6D, the pressure wave (23) can oscillate between a positive pressure amplitude (25) and a negative pressure amplitude (26) (as shown in the example of FIG. 4A through FIG. 4E), correspondingly increasing and decreasing the external ear canal pressure (7) relative to the ambient pressure (8) to alleviate a disorder symptom or treat a disorder. As to other particular embodiments, the pressure wave (23) can oscillate within only positive pressure amplitudes (25) in a range of between 0 kilopascals to about +50 kilopascals (as shown in the example of FIG. 5A through FIG. 5D), which can correspondingly increase the external ear canal pressure (7) relative to the ambient pressure (8) to alleviate a disorder symptom or treat a disorder. As to yet other particular embodiments, the pressure wave (23) can oscillate within only negative pressure amplitudes (26) in a range of between about −50 kilopascals to 0 kilopascals (as shown in the example of FIG. 6A through FIG. 6D), which can correspondingly decrease the external ear canal pressure (7) relative to the ambient pressure (8) to alleviate a disorder symptom or treat a disorder.

Again referring primarily to FIG. 4A through FIG. 6D, the pressure wave (23) can have a numerous and wide variety of waveforms, depending upon the application, corresponding to the numerous and wide variety of symptoms which can be alleviated or disorders which can be treated by the inventive method. As illustrative examples, the pressure wave (23) can be sine wave having smooth repetitive periodic oscillations (as shown in the example of FIG. 4A), a square wave in which the pressure amplitude (19) alternates at a steady frequency between fixed minimum and maximum values (as shown in the example of FIG. 4B), a rectangular wave, a trapezoidal wave or a truncated wave in which the apex of the pressure wave (23) has a constant pressure amplitude (19) over a time period (15) (as shown in the example of FIG. 4B in broken line, FIG. 5B, FIG. 5D, FIG. 6B, and FIG. 6D), a triangle wave having linear leading and trailing edges (as shown in the example of FIG. 4C, FIG. 5A, and FIG. 6A), a sawtooth wave in which either the leading edge changes pressure amplitude (19) over a time period (15) which is greater than the time period (15) in which the trailing edge changes pressure amplitude (19) (as shown in the example of FIG. 4D and FIG. 4E), or combinations thereof (as shown in the example of FIG. 5C and FIG. 6C).

Now referring primarily to FIG. 2, particular embodiments of the inventive method can further include moving a tympanic membrane (22) which lies across the external ear canal (12) to separate the external ear canal (12) from a middle ear (27) in response to achieving an external ear canal pressure differential (9) between the external ear canal pressure (7) and the ambient pressure (8) to alleviate a disorder symptom or treat a disorder. The tympanic membrane (22) is comprised of three layers, including an intermediate layer (lamina propria) which is disposed between an external epidermal layer and an internal mucosal layer. The intermediate layer includes modified mechanioreceptive vaterpacinian corpuscles ("mechanoreceptors"), which can be sensitive to deformation or stretch of the tympanic membrane (22). As such, these mechanoreceptors can function as baroreceptors and transmit afferent signals to the central nervous system associated with inward ("toward the middle ear") or outward ("away from the middle ear") movement of the tympanic membrane (22).

Figure 3A:
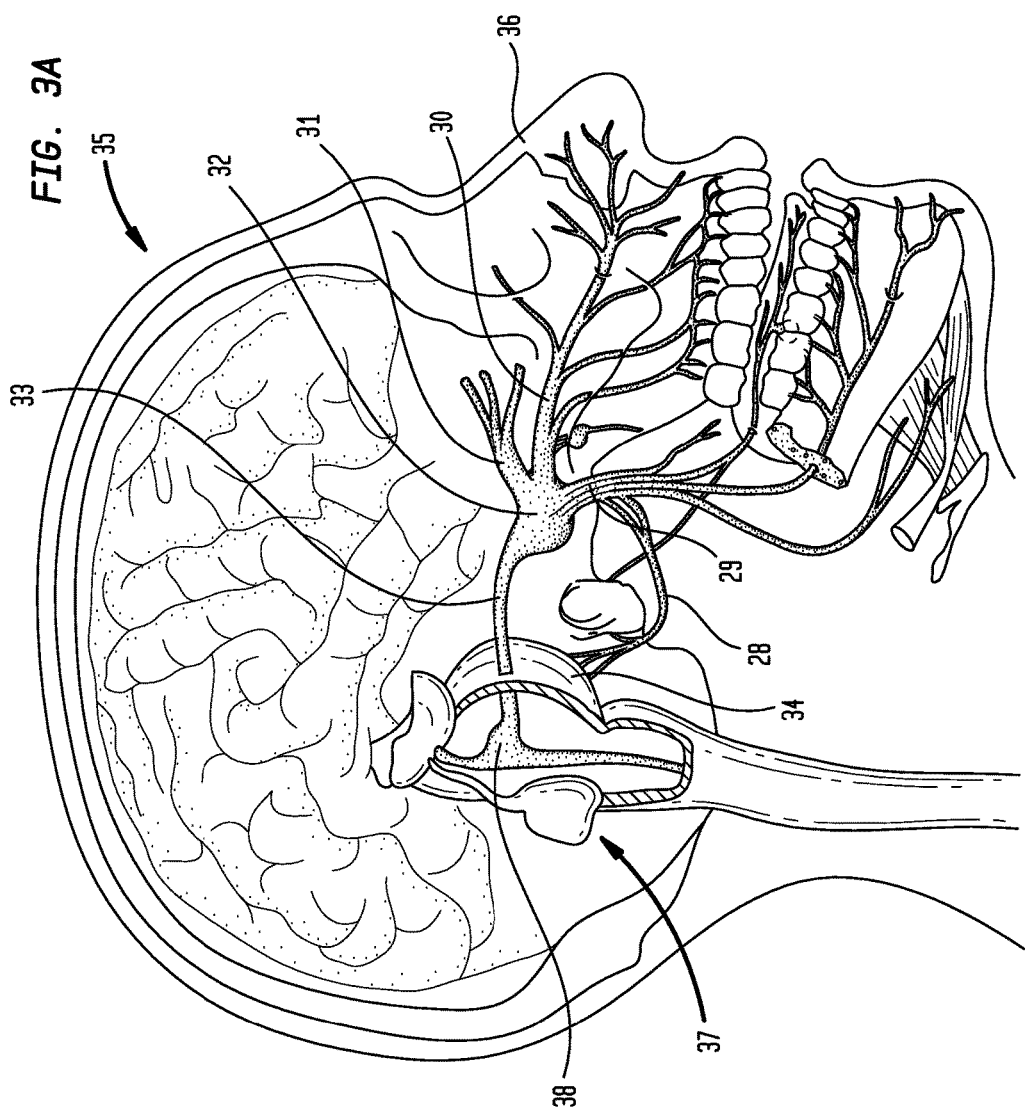
FIG. 3A is an illustration of anatomical features, including the trigeminal nerve, which can be acted upon by particular embodiments of the inventive method.
Figure 3B:
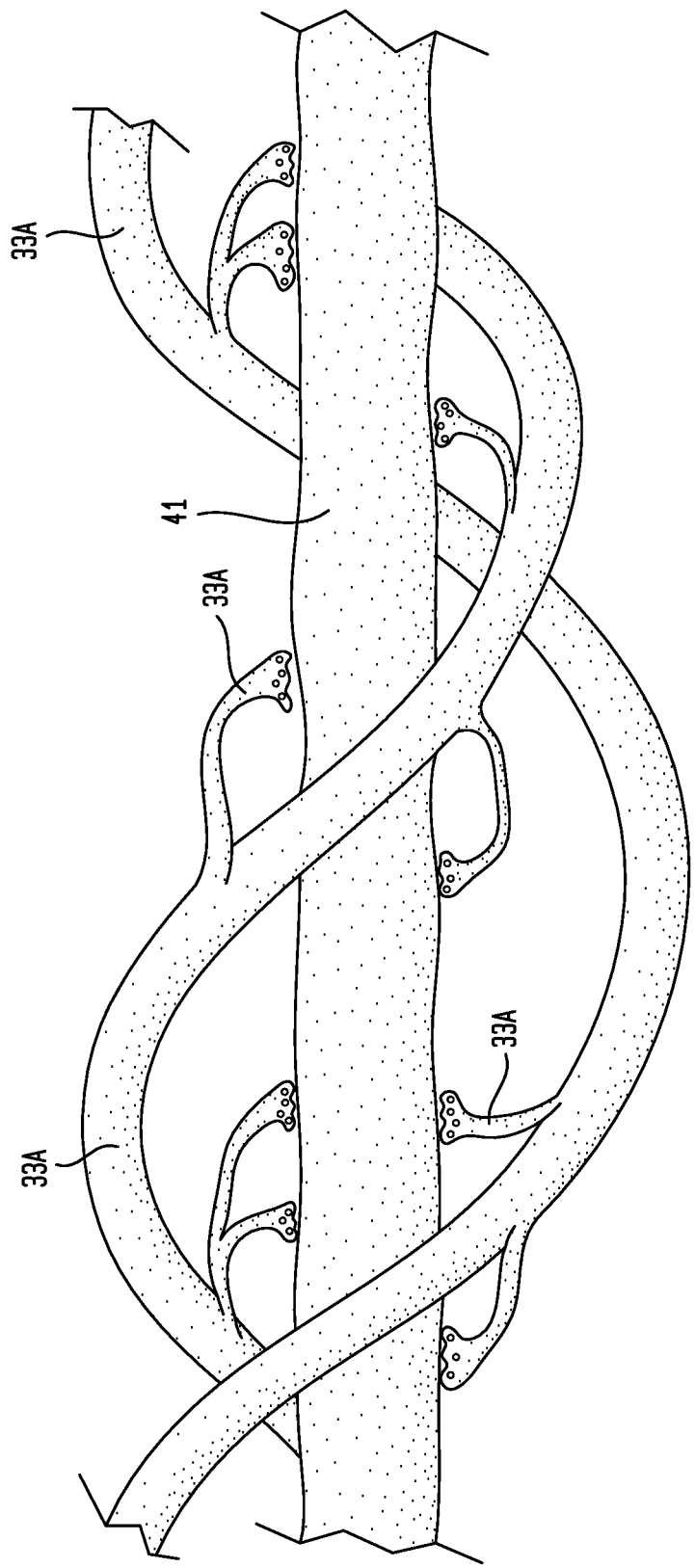
FIG. 3B is an enlargement of a portion of the trigeminal nerve and associated cranial vasculature which can be acted upon by particular embodiments of the inventive method.
Figure 6A:
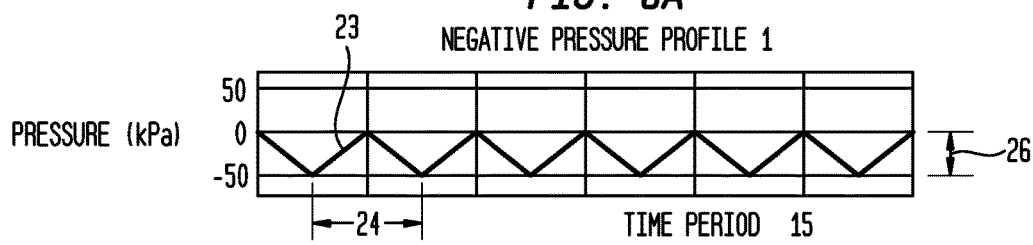
FIG. 6A is a graph of a negative pressure regulation profile useful in a particular embodiment of the inventive method.
Figure 6B:
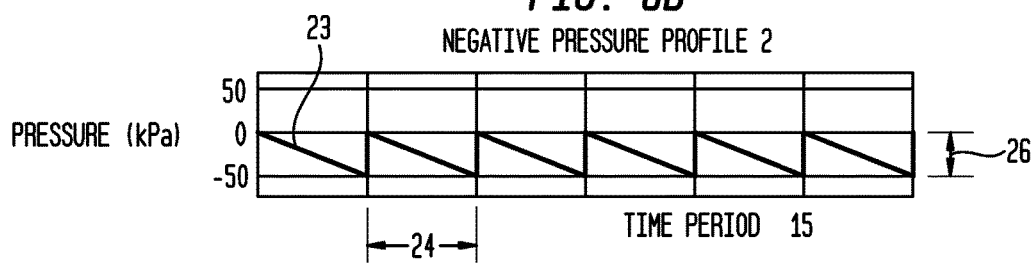
FIG. 6B is a graph of a negative pressure regulation profile useful in a particular embodiment of the inventive method.
Figure 6C:
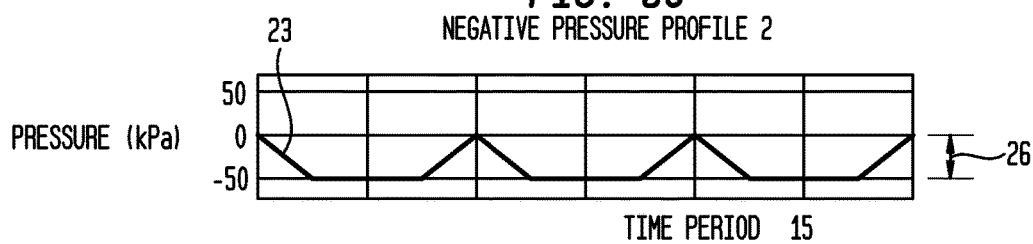
FIG. 6C is a graph of a negative pressure regulation profile useful in a particular embodiment of the inventive method.
Figure 6D:
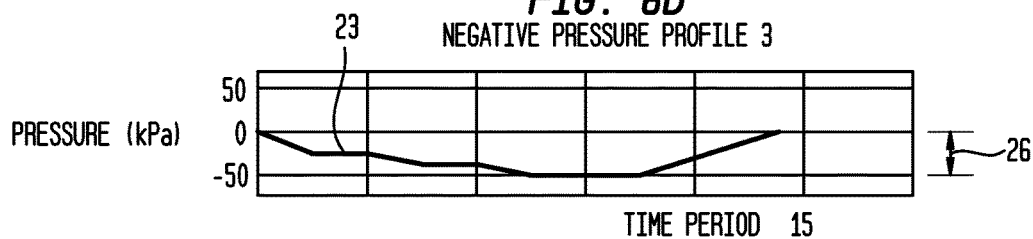
FIG. 6D is a graph of a negative pressure regulation profile useful in a particular embodiment of the inventive method.
Figure 6E:
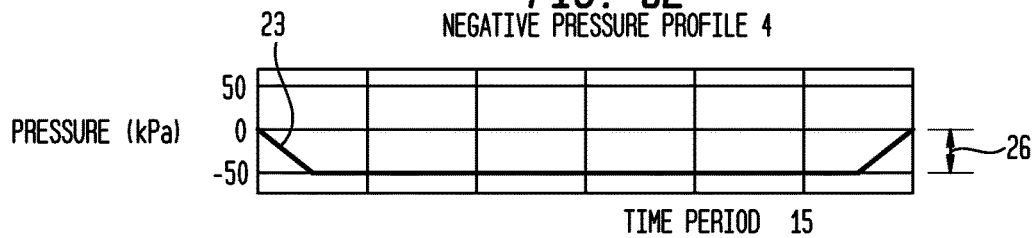
FIG. 6E is a graph of a negative pressure regulation profile useful in a particular embodiment of the inventive method.

Now referring primarily to FIG. 3A, the mechanoreceptors can transmit the afferent signals to the auriculotemporal nerve (28) via A-β pseudounipolar fibers, which subsequently merges with the mandibular nerve (29). The mandibular nerve (29) converges with the maxillary nerve (30) and the ophthalmic nerve (31) to form the trigeminal ganglion (32), where the cell bodies of the primary afferent pressure-conveying fibers reside. The afferent fibers are conveyed through the sensory root of the trigeminal nerve (33) to the ventrolateral aspect of the midbelly of the pons (34). In this way, the trigeminal nerve (33) can transmit sensory signals including nociceptive signals ("pain signals") from the cranium (35) and face (36) to the central nervous system. The afferent fibers then enter the brainstem (37) and synapse on various parts of the trigeminal nuclear system (38), including the deep lamina of the Trigeminal Nucleus Caudalis, where the afferent fibers can induce GABAergic interneurons to hyperpolarize nociceptive fibers and interneurons in the superficial laminae to block nociceptive transmission. In accordance with the inventive method described herein, an external ear canal pressure differential (9) between the external ear canal pressure (7) and the ambient pressure (8) can induce an anti-nociceptive barrage of mechanoreceptor-derived neural impulses such that the various related nuclei of the brainstem pain matrix can become attenuated and resume normal, steady-state activity. Also, parasympathetically-induced intracranial vasodilation can cease, restoring resting vascular flow and tone within the cranial vasculature (41), a portion of which can be associated with the trigeminal nerve (33) and trigeminal nerve fibers (33A) as part of the trigeminal system, as shown in the example of FIG. 3B. In addition to modulating vascular dynamics, biochemical alterations can be induced, such as a down-regulation of inflammatory cytokines or other pain-promoting compounds within or around the cranial vascular beds, whereby the vascular normalization can lead to further quiescence of trigeminal nociceptive afferentation which can culminate in the alleviation of a disorder symptom or the resolution of a disorder.

Now referring primarily to FIG. 2, particular embodiments of the inventive method can further include moving a tympanic membrane (22) toward the middle ear (27), thus increasing the concavity of the tympanic membrane lateral surface (39), which can be achieved by a positive external ear canal pressure differential (17) between the external ear canal pressure (7) and the ambient pressure (8) to alleviate a disorder symptom or treat a disorder. Also, the tympanic membrane (22) can be moved away from the middle ear (27), thus decreasing the concavity of the tympanic membrane lateral surface (39), which can be achieved by a negative external ear canal pressure differential (18) between the external ear canal pressure (7) and the ambient pressure (8) to alleviate a disorder symptom or treat a disorder. As to particular embodiments, the tympanic membrane (22) can be moved toward or away from the middle ear (27) one or a plurality of times during the inventive method. As an illustrative example, the tympanic membrane (22) can be reciprocally moved with a movement amplitude and a movement frequency, both of which can be driven by the pressure wave (23) in the external ear canal (12) over the time period (15) that the inventive method is applied.

The inventive method can further include moving the tympanic membrane (22) to stimulate the mechanoreceptors, which can alleviate a disorder symptom or treat a disorder. As to particular embodiments, moving the tympanic membrane (22) can generate a nerve signal which can decrease transmission of a nociceptive signal to the central nervous system, which can result in analgesic stimulation of the central nervous system. The inventive method can further include altering the movement amplitude and the movement frequency of the tympanic membrane (22) to counteract central nervous system habituation.

Again referring primarily to FIG. 2, particular embodiments of the inventive method can further include flowing a fluid volume (40) within the external ear canal (12). The fluid volume (40) can be a predetermined fluid volume (40), typically in a range of between 0 milliliters to about 20 milliliters; however, embodiments can have a lesser or greater fluid volume (40) depending upon the application. As to particular embodiments, one or more fluid volumes (40) can be selected from the group including or consisting of: between 0 milliliters to about 2 milliliters, between about 1 milliliter to about 3 milliliters, between about 2 milliliters to about 4 milliliters, between about 3 milliliters to about 5 milliliters, between about 4 milliliters to about 6 milliliters, between about 5 milliliters to about 7 milliliters, between about 6 milliliters to about 8 milliliters, between about 7 milliliters to about 9 milliliters, between about 8 milliliters to about 10 milliliters, between about 9 milliliters to about 11 milliliters, between about 10 milliliters to about 12 milliliters, between about 11 milliliters to about 13 milliliters, between about 12 milliliters to about 14 milliliters, between about 13 milliliters to about 15 milliliters, between about 14 milliliters to about 16 milliliters, between about 15 milliliters to about 17 milliliters, between about 16 milliliters to about 18 milliliters, between about 17 milliliters to about 19 milliliters, and between about 18 milliliters to about 20 milliliters. The one or more fluid volumes (40) desired for use in particular embodiments of the inventive method can be influenced by such factors as auditory meatus anatomy, physiology, or biochemistry; disorder symptom targeted for alleviation; disorder targeted for treatment; observable effect(s) of the inventive method; or the like; or combinations thereof; but not so much as to cause discomfort to a user (20) or injury to the auditory meatus (21) or the tympanic membrane (22).

As to particular embodiments, the inventive method can further include flowing a plurality of predetermined fluid volumes (40) within the external ear canal (12), each one of the plurality of predetermined fluid volumes (40) capable of altering the external ear canal pressure differential (9) between the external ear canal pressure (7) and the ambient pressure (8) to alleviate a disorder symptom or treat a disorder. By flowing the plurality of predetermined fluid volumes (40) within the external ear canal (12), the pressure amplitude (19) of the external ear canal pressure differential (9) can be regulated. As an illustrative example, flowing a greater fluid volume (40) within the external ear canal (12) can result in a greater external ear canal pressure differential (9) whereas flowing a lesser fluid volume (40) within the external ear canal (12) can result in a lesser external ear canal pressure differential (9). As to particular embodiments, modulating the pressure amplitude (19) of the external ear canal pressure differential (9) can include generating a pressure wave (23) having a pressure wave frequency (24) which can drive a reciprocal fluid flow (2) of a fluid (3) in the external ear canal (12) over a time period (15). As to particular embodiments including flowing a fluid volume (40) within the external ear canal (12), the inventive method can further include moving the tympanic membrane (22) toward the middle ear (27) or away from the middle ear (27) in response to the fluid volume (40).

In addition to achieving an external ear canal pressure differential (9) between the external ear canal pressure (7) and the ambient pressure (8), particular embodiments of the inventive method can further include, whether prior to or subsequent to regulating the external ear canal pressure differential (9), and as to certain embodiments without regulating the external ear canal pressure differential (9), adjusting a temperature of the fluid (3) to a fluid temperature (42) which can be lesser than or greater than a body temperature (43). Typically, the fluid temperature (42) can be adjusted in a range of between 10 degrees Celsius to about 50 degrees Celsius; however, embodiments can have a lesser or greater fluid temperature (42) depending upon the application. As to particular embodiments, one or more fluid temperatures (42) can be selected from the group including or consisting of: between about 10 degrees Celsius to about 20 degrees Celsius, between about 15 degrees Celsius to about 25 degrees Celsius, between about 20 degrees Celsius to about 30 degrees Celsius, between about 25 degrees Celsius to about 35 degrees Celsius, between about 30 degrees Celsius to about 40 degrees Celsius, between about 35 degrees Celsius to about 45 degrees Celsius, and between about 40 degrees Celsius to about 50 degrees Celsius. The one or more fluid temperatures (42) desired for use in particular embodiments of the inventive method can be influenced by such factors as auditory meatus anatomy, physiology, or biochemistry; disorder symptom targeted for alleviation; disorder targeted for treatment; observable effect(s) of the inventive method; or the like; or combinations thereof; but not so much as to cause discomfort to a user (20) or injury to the auditory meatus (21) or the tympanic membrane (22).

Again referring primarily to FIG. 2, the inventive method can further include modulating a vestibular endolymph temperature (44) of vestibular endolymph (45) within a membranous labyrinth (46) of an inner ear (47). The viscosity of the vestibular endolymph (45) can enable movement of the head or body to proportionately displace the vestibular endolymph (45) within the membranous labyrinth (46), which can generate neural signals to convey the movement of the head or body to the brain. As to particular embodiments, the inventive method can further include stimulating movement of the vestibular endolymph (45) within the membranous labyrinth (46) of the inner ear (47). Convective movement of the vestibular endolymph (45) or disruption of abnormal vestibular endolymph (45) endolymph stasis can further be promoted by mechanical pulses transmitted through the ossicular chain to the oval window or via middle ear (27) pressure changes transmitted to the round window of the cochlea.

As to particular embodiments which include adjusting the fluid temperature (42), the inventive method can further include fluidicly coupling the external ear canal (12) to the ambient pressure (8) and circulating the fluid flow (2) of the fluid (3) through the earplug (4) within the external ear canal (12). As to particular embodiments, the fluid temperature (42) can be maintained as a constant fluid temperature (42) over a time period (15) or can be varied over the time period (15).

The inventive method described herein can be applied once or can be repeated a plurality of times. For example, if a user (20) reports a favorable response, application of the inventive method can be continued or repeated. Alternatively, application of the inventive method can be discontinued if a favorable response is not observed. Regardless of the response, the inventive method can further include disengaging the earplug (4) from the external ear canal wall (6).

Typically, but not necessarily, the inventive method can be applied to the ear (14) disposed on the side of the head that is most affected by a symptom or a disorder; however, the inventive method can be applied to both ears (14), either simultaneously or sequentially, depending upon the application. Accordingly, the inventive method can further include achieving an external ear canal pressure differential (9) between the external ear canal pressure (7) and the ambient pressure (8) in a plurality of external ear canals (12) to alleviate a disorder symptom or treat a disorder. As to particular embodiments, one fluid transfer device (1) can be provided which can generate the fluid flow (2) of a fluid (3) through each of a plurality of earplugs (4) corresponding to each of the plurality of external ear canals (12) to achieve similar or dissimilar external ear canal pressure differentials (9) between the external ear canal pressure (7) of each of the plurality of external ear canals (12) and the ambient pressure (8).

In addition to alleviating a disorder symptom or treating a disorder, the invention method can also be used to assist in diagnosing compromise to structures of the middle ear (27) or inner ear (47), such as superior canal dehiscence or perilymphatic fistula.

Figure 7A:
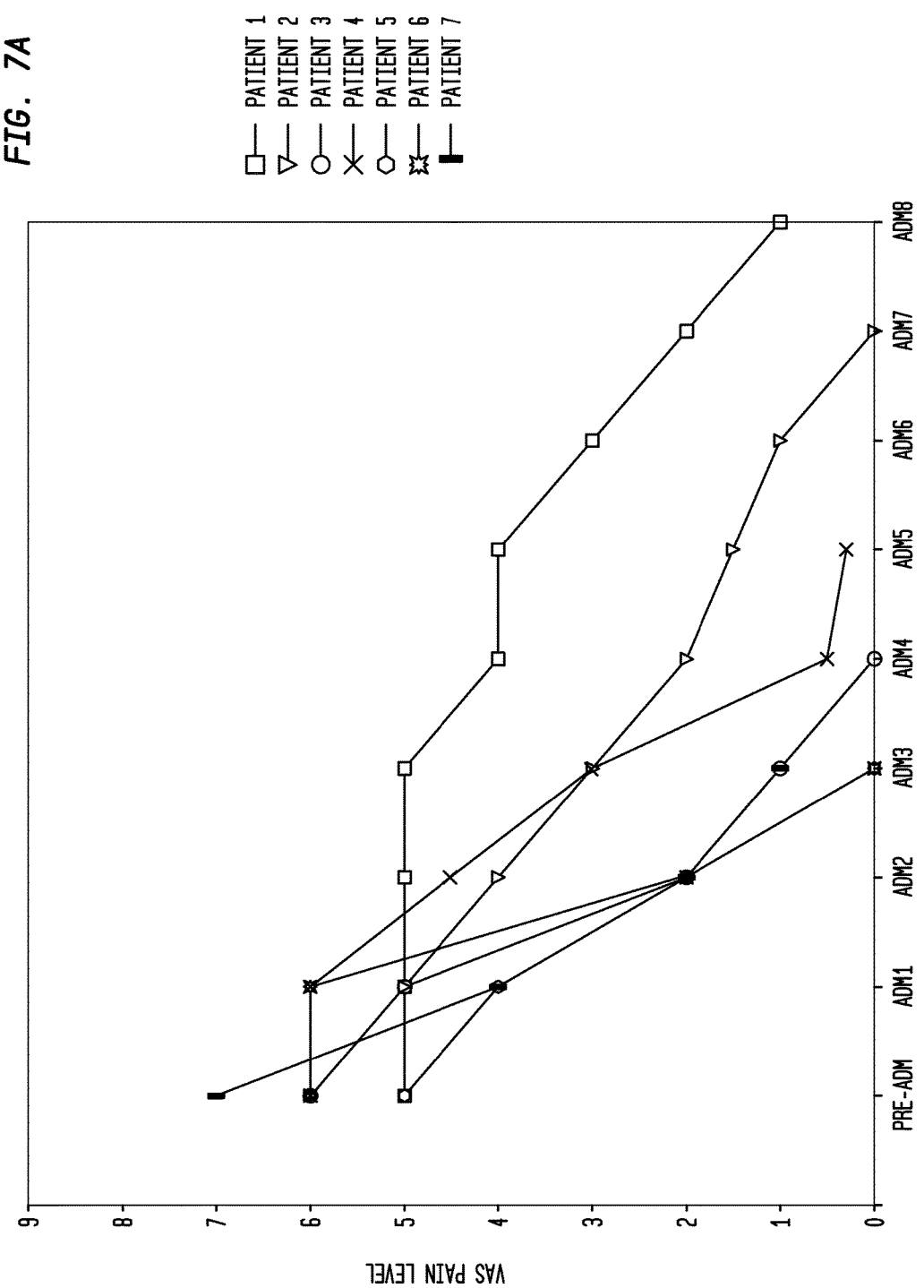
FIG. 7A is a graph which plots the results achieved in seven patients using a particular embodiment of the inventive method to alleviate symptoms of a disorder.
Figure 7B:
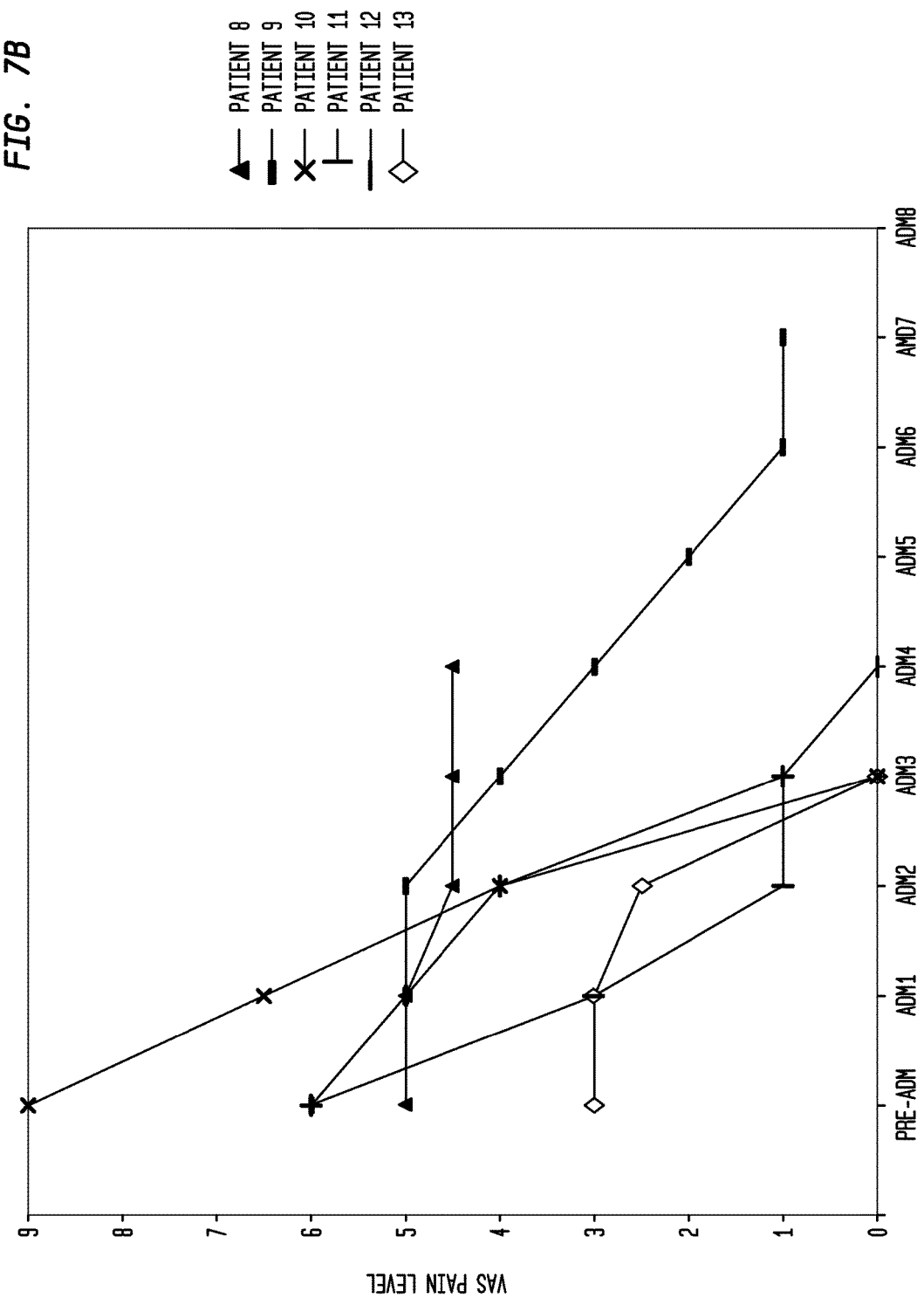
FIG. 7B is a graph which plots the results achieved in six patients using a particular embodiment of the inventive method to alleviate symptoms of a disorder.

Now referring primarily to FIG. 7A and FIG. 7B, which are graphs evidencing the results of the administration of the inventive method to thirteen patients. The results are plotted as visual analog pain ("VAS Pain Level") against round of administration ("Tx"). In the investigation, the inventive method was administered to thirteen patients as above described and using the particular embodiment of the inventive method described below in Example 1 through Example 13.

As to each of Example 1 through Example 13, primarily for purposes of patient comfort and ease of administration, each patient was placed in a supine position with their head slightly elevated. Patients remained in this position for roughly three minutes, in order to acclimate to the supine position, lighting, and environmental conditions. The patient's eyes remained open for the duration of the administration of the inventive method.

Each patient was asked to rate their level of pain prior to the administration of the inventive method ("pre-administration") (shown as "Pre-Adm" in the graph of FIG. 7A and FIG. 7B), after each subsequent administration of the inventive method ("Admn"), at the completion of the administration of the inventive method ("post-administration"), and at thirty minutes following the administration of the inventive method ("thirty minutes post-administration"), at four hours following the administration of the inventive method ("four hours post-administration"), and at twenty-four hours following the administration of the inventive method ("twenty-four hours post-administration"). Pain was rated with a visual analog scale ("VAS") with zero representing no pain at all and ten representing the highest possible level of pain.

In order to validate the difference between the inventive method and a sham method, some patients were first administered successive 30-second rounds of fluid transfer device (1) placement in the external ear canal (12) with no adjustment of external ear canal pressure (7).

The embodiment of the inventive method administered included a fluid transfer device (1) having a pneumatic otoscope fitted with a 7.0 mm diagnostic reusable speculum and an insufflator bulb. The embodiment of the inventive method was administered in roughly 30-second intervals to the ear (14) on the side of the head that was most symptomatic. Multiple rounds of pneumatic insufflation were administered. The external ear canal pressure (7) applied produced observable deflection of the tympanic membrane (22), but not so much as to cause discomfort. A pulsatile pressure amplitude (19) was applied at a pressure wave frequency (24) of approximately two Hertz. If the patient reported a continued and positive response with each administration, the inventive method was continued in order to determine the extent to which a symptom(s) could be alleviated or a disorder (s) could be treated. Administration of the inventive method was discontinued when there was no change in a disorder symptom(s) or a disorder for three consecutive rounds of administration of the inventive method.

EXAMPLE 1

Patient number 1 was a right-handed, 38-year-old female. Her pertinent history of migraine included ten years of severe migraines occurring around twenty days per month. Previous magnetic resonance imaging (MRI) evaluation revealed early degenerative disc changes at C5-6 and no abnormalities detected in the brain. Her current pharmaceutical regimen pertaining to migraine consisted of sumatriptan 100 mg at the onset of symptoms. She reported that if she would fail to take sumatriptan in the earliest stages of her headache, the pain would quickly escalate and become refractory to any interventions, typically leading to emergency medical care. Pre-administration neurologic exam revealed light and sound sensitivity as well as tactile allodynia on the left side of her face and neck. She also reported having aura and nausea. She reported that she had not taken any prescription drugs or other over-the-counter remedies within the last eight hours for the current headache. Her pre-administration rating of pain on a visual analog scale was 5/10.

Patient number 1 was administered the sham method first. She reported VAS scores of 5/10 before and 5/10 after, so the sham method was discontinued. She was then administered the inventive method. Over successive rounds of administration of the inventive method, her VAS pertaining to face/head pain was 5/10, 5/10, 5/10, 4/10, 4/10, 3/10, 2/10, and 1/10. VAS scores pertaining to neck pain were 5/10, 5/10, 5/10, 5/10, 5/10, 5/10, 4/10, 3/10, 3/10, and 3/10. Total administration time was approximately twelve minutes. Post-administration neurological exam revealed the absence of light and sound sensitivity and she reported that her nausea had resolved. At thirty minutes post-administration, her VAS was 0/10 (face) and 1/10 (neck). Four hours post-administration, she reported a slight recurrence of pain; 1/10 (face) and 2/10 (neck). At twenty-four hours post-administration, she reported a VAS of 1/10 (face) and 2/10 (neck). There was no incidence of vertigo, nystagmus or aberrant autonomic response.

EXAMPLE 2

Patient number 2 was a right-handed, 38-year-old female. Her pertinent history of migraine included twenty-five years of almost daily migraine with aura. Her previous treatments for headaches included occipital nerve stimulator, occipital nerve blocks and botulinum toxin injections. Previous imaging of the brain was negative. Pre-administration neurologic exam revealed light sensitivity and tactile allodynia around the left occipital and temporal areas. She reported aura, flashes/floaters and smell sensitivity. Her current pharmaceutical regimen pertaining to migraine included over-the-counter medications, SSRIs and dopamine reuptake inhibitors. She reported that she had not taken any prescription drugs or other over-the-counter medications within the last eight hours for this current headache. Her pre-administration rating of pain on a visual analog scale was 6/10.

She was administered the inventive method first. Over successive rounds of administration of the inventive method, her VAS was 5/10, 4/10, 3/10, 2/10, 1.5/10, 1/10, and 0/10. Total administration time was approximately twelve minutes. Thirty minutes after administration, her VAS score was 5/10. At four hours post administration and twenty-four hours post administration, her VAS scores were 4/10. Her post-administration neurological exam revealed the absence of light sensitivity and tactile allodynia. She reported that her aura had completely resolved as well. There was no incidence of vertigo, nystagmus or aberrant autonomic response.

EXAMPLE 3

Patient number 3 was a right-handed, 33-year-old female. Her previous history of migraine included seventeen years of recurrent migraine of moderate to severe intensity. She denied using triptans or having any surgical interventions for headache. MRI of the head was unremarkable. The current headache was encompassing the left eye and frontal area, and had a sharp, throbbing nature. Light touch in that area provoked a pain response. She reported aura, nausea and vomiting occasionally through the day. Her current pharmaceutical regimen pertaining to migraine included over-the-counter migraine medications at the onset of symptoms. She reported that she had taken other over-the-counter medications approximately six hours previously for the current headache. Her pre-administration rating of pain on a visual analog scale was 6/10.

She was administered the sham method first. The patient reported VAS scores of 6/10 before and 6/10 after, so the sham method was discontinued. She was then administered the inventive method. Over successive rounds of administration of the inventive method, her VAS scores were 5/10, 2/10, 1/10, and 0/10. Total administration time was approximately six minutes. At thirty minutes post-administration, her VAS was 5/10. At both four hours post-administration and twenty-four hours post-administration, her VAS scores were 4/10. Her post-administration neurological exam revealed the absence of light sensitivity and tactile allodynia. She reported that her aura and nausea had completely resolved as well. There was no incidence of vertigo, nystagmus or aberrant autonomic response.

EXAMPLE 4

Patient number 4 was a right-handed, 43-year-old female. Her pertinent history of migraine included twenty years of recurrent migraine with aura occurring approximately six days per month. Her previous treatments for migraine included sumatriptan for prophylaxis and acute treatment. Previous imaging of the head and brain were negative. During her migraines, she would experience aura, flashes/floaters, nausea, pulsing pain, and light, sound, and smell sensitivity. Her current pharmaceutical regimen pertaining to migraine included over-the-counter ibuprofen 400 mg as needed. She reported that she had not taken any prescription drugs or other over-the-counter medications within the last eight hours for this current headache, which was present upon awakening that morning. The headache she was experiencing at the time of administration consisted of a squeezing pressure around the temples and the base of the skull. She reported that the headache was building in intensity and would most likely develop into a full-blown migraine in the coming hours. Her pre-administration rating of pain on a visual analog scale was 6/10.

She was administered the inventive method to the left ear, because she would typically experience her migraine symptoms on the left side of her head. Over successive rounds of administration of the inventive method, her VAS scores were 6/10, 4.5/10, 3/10, 0.5/10, and 0.2/10. Total administration time was approximately ten minutes. At thirty minutes post-administration, her VAS was 0.5/10. At four hours post-administration, her VAS was 0.5/10 and at twenty-four hours post-administration, her VAS was 0/10. She reported that there was virtually no pain post-administration and that she felt extremely relaxed and calm. There was no incidence of vertigo, nystagmus or aberrant autonomic response.

EXAMPLE 5

Patient number 5 was a right-handed, 25-year-old female. She did not report a significant past history of migraine, although she presented with "the worst headache of [her] life". She described a severe headache of five days duration which had a throbbing, pulsatile nature to it. She also reported dizziness and sensitivity to light and sound associated with her headache. She stated that the headache spanned the front of her forehead, temples and the base of her head with vice-like pressure. She reported that she had taken ibuprofen and acetaminophen earlier in the day, approximately six hours previously. Those medications helped to reduce her pain level from 9/10 on a VAS to her pre-administration rating of 5/10.

She was administered the sham method first. The patient reported VAS scores of 5/10 before and 5/10 after, so the sham method was discontinued. She was then administered the inventive method. Because she did not have a unilateral headache, the right ear was arbitrarily chosen as the initial side of administration of the inventive method. Over successive rounds of administration of the inventive method, her VAS scores pertaining to right sided pain were 4/10, 2/10, and 0/10. The pain remained unchanged in the left side of her head. She was then administered the inventive method to the left ear. Her pre-administration rating of pain on the left was 5/10. Over successive rounds of administration, her VAS scores pertaining to left sided pain were 4/10, 3/10, 1/10, 1/10, and 0.5/10. Total administration time was approximately twelve minutes. At thirty minutes post-administration, her VAS was 1/10 and was 0/10 at four hours post-administration and 0/10 at twenty-four hours post-administration. There was no incidence of vertigo, nystagmus or aberrant autonomic response.

EXAMPLE 6

Patient number 6 was a right-handed, 30-year-old female. Her pertinent history of migraine included fifteen years of recurrent migraine. She experienced migraine headaches approximately thirty days per month and reported experiencing significant limitations and disability due to migraine. Her previous use of pharmacological agents for headaches included eletriptan and over-the-counter migraine medications. She described the current headache as severe and present for the past twenty-four hours. Pre-administration neurologic exam revealed light sensitivity and tactile allodynia at the forehead and temples. She also reported dizziness and nausea. She reported that the headache had been localized to the left side of her face and head, but had evolved to encompass both sides of the forehead, temples and base of her head. She reported that she had taken over-the-counter migraine medication four hours previously and it had no effect. She took a second dose thirty minutes later and it brought her pain level down from a 10/10 to a 4/10. Her pre-administration rating of pain on a VAS was 6/10 and she rated her nausea as a 7/10.

Patient number 6 was administered the inventive method to the left ear first. Over successive rounds of administration, her VAS scores pertaining to face/head pain were 6/10, 2/10, 0/10, and 0/10. VAS scores pertaining to nausea were 7/10, 0/10, 0/10, and 0/10. Total administration time was approximately six minutes. Her post-administration neurological exam revealed the absence of light sensitivity and tactile allodynia. She reported a complete resolution of pain and nausea. At thirty minutes post-administration, her VAS was 0/10 (pain) and 0/10 (nausea). Four hours post-administration, she reported a VAS of 0/10 for both pain and nausea. At twenty-four hours post-administration, she reported a VAS of 0/10 for both pain and nausea. There was no incidence of vertigo, nystagmus or aberrant autonomic response.

EXAMPLE 7

Patient number 7 was a right-handed, 39-year-old female. Her history of migraine included twenty-seven years of recurrent migraine. She experienced migraine headaches approximately twenty days per month and reported 'severe' impact on quality of life due to migraine headaches. Her current use of pharmacological agents for migraine included topiromate, sumatriptan and duloxetine. She had also undergone two botulinum toxin injections in the past seven months. She described the current headache as severe and present for the past three to four days. Pre-administration neurologic exam revealed light sensitivity, slight dysarthria and tactile allodynia at the forehead and temples bilaterally. She also reported dizziness, nausea, unsteadiness with walking, left ptosis, slurred speech and sensitivity to light, sound and smell. She stated that the headache had been localized to the right side of her face and head, but had evolved to encompass both sides of the forehead, temples, top and base of her head. She reported that she had taken sumatriptan two days previous and approximately six hours previously. Her pre-administration rating of pain on a VAS was 7/10.

She was first administered the inventive method to the right ear. Over successive rounds of administration, her VAS scores pertaining to pain were 4/10, 2/10, and 1/10 with some pain remaining at the left eye. Administration was then directed to the left ear. One thirty-second round of administration to the left ear abolished the remaining pain at the left eye. Because she noted some slight pain to palpation at the right forehead (1/10), therapy was conducted again at the right ear. One 30-second round of administration abolished all remaining pain at the right forehead. Total administration time was approximately twelve minutes. She reported being completely free of nausea, pain, sensitivities, and there were no detectable abnormalities in speech. She reported that her unsteady gait had returned to normal as well. At thirty minutes post-administration, her VAS was 0/10 and was 1/10 at four hours post-administration and 3/10 at twenty-four hours post-administration. There was no incidence of vertigo, nystagmus or aberrant autonomic response.

EXAMPLE 8

Patient number 8 was a right-handed, 53-year-old female. Her history of migraine included thirty years of recurrent migraine. She experienced migraine headaches approximately six days per month and reported 'moderate' impact on quality of life due to migraine headaches. Her current use of pharmacological agents for migraine included citalopram, sumatriptan, ibuprofen and naproxen. She described the current headache as moderate and fluctuating between mild to severe over the past seven days. The pain had become slightly worse over the previous thirty-six hours and she reported feeling as though the pain was starting to abate and resolve. Pre-administration neurologic exam revealed light sensitivity and slight tactile allodynia at the left forehead. She reported nausea as a feature of the current headache and that the headache had been localized to the left side of her face and head. She reported that she had taken sumatriptan one-day and four-days previous. Her pre-administration rating of pain on a VAS was 5/10.

She was first administered the inventive method to the left ear. Over successive rounds of administration, her VAS scores pertaining to pain were 5/10, 4.5/10, 4.5/10 and 4.5/10. Because her pain level had been unchanged over three successive rounds, administration of the inventive method was discontinued and she was released. At thirty minutes post-administration, her VAS was 6/10 and was 3/10 at four hours post-administration and 1/10 at twenty-four hours post-administration. There was no incidence of vertigo, nystagmus or aberrant autonomic response.

EXAMPLE 9

Patient number 9 was a right-handed, 47-year-old female. Her history of migraine included five years of recurrent migraine. Her primary issue was chronic daily headache of varying severity and migraine headaches approximately four days per month. She reported 'moderate' impact on quality of life due to migraines and chronic daily headaches and she could not recall any time in the previous twelve months that her pain was completely absent. Her current use of pharmacological agents for migraine included topiromate 200 mg daily, wellbutrin and over-the-counter migraine medication as needed. In the past four years, she had utilized physical therapy extensively and to a lesser extent, chiropractic adjustments and acupuncture, all with limited to no relief. Pre-administration neurologic exam revealed light and sound sensitivity. There was no tactile allodynia present at the time of investigation, although she has experienced that as a feature of her migraines. She did report nausea of a moderate to intense degree. She stated that the current headache encompassed the whole head with pressure and throbbing at the forehead, temples, top and base of her head. She reported that she had not taken any medication in the previous twenty-four hours. Her pre-administration rating of pain on a VAS was 6/10 over the whole head.

She was first administered the inventive method to the left ear because she would typically experience her migraine headaches on that side. Over successive rounds of administration, her VAS scores pertaining to pain were 5/10 (bilateral), 5/10 (bilateral), 4/10 (left)-5/10 (right), 3/10 (left)-4/10 (right), 2/10 (left)-3/10 (right), 1/10 (left)-3/10 (right), and 1/10 (left)-3/10 (right). The inventive method was then administered once to the right ear which had no effect, pain levels remained at 1/10 (left)-3/10 (right). One final administration was applied to the left ear and resulted in VAS of 0/10 (left)-2/10 (right). The only remaining pain was a slight irritation at the posterior aspect on the right side of her head. Total administration time was approximately thirty minutes. Upon questioning, she reported a 90% improvement in her nausea. At thirty minutes post-administration, her VAS was 0/10 (left)-2/10 (right), 1/10 (left)-2/10 (right) at four hours post-administration, and 1/10 (left)-2/10 (right) at twenty-four hours post-administration. There was no incidence of vertigo, nystagmus or aberrant autonomic response.

EXAMPLE 10

Patient number 10 was a right-handed, 37-year-old female. Her history of migraine included thirty-two years of recurrent migraine. She would experience migraine headaches approximately twelve days per month and would be generally incapacitated during those days. She reported 'severe' impact on quality of life due to her migraines. Her current use of pharmacological agents for migraine included tramadol 400 mg daily, duloxetine 120 mg daily, fioricet and fioricet with codeine. Her previous use of medication included prochlorperazine, hydromorphone with promethazine, and in extreme situations, she would be treated with a combination of meperidine, ketorolac and promethazine. She had also undergone occipital nerve block three years previously which did not have any positive effect on her pain. Past MRI examination of the head revealed no abnormalities. Pre-administration neurologic exam revealed light and sound sensitivity. There was no tactile allodynia present at the time of investigation, although she would frequently experience that as a feature of her migraines. She did report nausea of a moderate degree. She stated that the current headache was primarily centered around the left occipital area with some radiation to the left temple and was present for the last three days. She reported that she had taken a dose of fioricet approximately five hours previously. Her pre-administration rating of pain on a VAS was 9/10.

Because she was experiencing her migraine on the left side of her head, she was first administered the inventive method to the left ear. Over successive rounds of administration of the inventive method, her VAS scores pertaining to pain were 6.5/10, 4/10, and 0/10. One final application was applied to the left ear and maintained her VAS of 0/10. She reported complete resolution of her light and sound sensitivity as well as her nausea. Total administration time was approximately fifteen minutes. At thirty minutes post-administration, her VAS was 0/10 and was 0/10 at four hours post-administration and 0/10 at twenty-four hours post-administration. There was no incidence of vertigo, nystagmus or aberrant autonomic response.

EXAMPLE 11

Patient number 11 was a right-handed, 53-year-old female. Her history of migraine included three years of recurrent migraine. She would experience migraine headaches approximately three days per month and would be unable to perform home or work duties during those days. She reported 'moderate' impact on quality of life due to her migraines. Her current use of pharmacological agents for migraine included ibuprofen as needed. Due to past history of cardiac ablation and chronic cardiac disease, she declined any more advanced pharmacological treatment. Pre-administration neurologic exam revealed light sensitivity. There was slight tactile allodynia present at the time of investigation. She did not report any nausea. She stated that the current headache had been present for approximately twenty hours and was primarily centered around the right eye and forehead. She stated that she had recently undergone a detoxification protocol which triggered the migraine event. She reported that she had not taken any medication for the current headache. Her pre-administration rating of pain on a VAS was 6/10.

Because she was experiencing her migraine on the right side of her head, she was first administered the inventive method to the right ear. Over successive rounds of administration, her VAS scores pertaining to pain were 3/10, 1/10, and 1/10. She reported complete resolution of her light sensitivity. Total administration time was approximately ten minutes. At thirty minutes post-administration, her VAS was 0/10 and was 3/10 at four hours post-administration, 6/10 at eight hours post-administration and 0/10 at twenty-four hours post-administration. There was no incidence of vertigo, nystagmus or aberrant autonomic response although she reported some tenderness at the auditory meatus.

EXAMPLE 12

Patient number 12 was a left-handed, 41-year-old female. Her history of migraine included twenty-nine years of recurrent migraine. She would experience migraine headaches approximately twenty days per month and would be mostly incapacitated during those days. She reported 'extreme' impact on quality of life due to her migraines. Her current use of pharmacological agents for migraine included venlaxafine HCL, verapamil, and rizatriptan. She had an extensive history of medication usage including amitriptyline, butalibital/floricet, multiple triptans, nortriptyline, topiramate, cyclobenzaprine, gabapentin and propranolol. Previous MRI of the brain showed no abnormalities. Pre-administration neurologic exam revealed light sensitivity. There was slight tactile allodynia present at the time of investigation. She did not report any nausea. She stated that the current headache had been present for approximately seven hours and encompassed both right and left temples and forehead. She reported blurry vision, speech abnormalities and sensitivity to lights, sounds and smells. She reported that she had not taken any medication for the current headache. Her pre-administration rating of pain on a VAS was 6/10.

Although she was experiencing her migraine on both sides of her head, she reported that she would typically experience more pain on the right side. She was administered the inventive method to the right ear. Over successive rounds of administration of the inventive method, her VAS scores pertaining to pain were 5/10, 4/10, 1/10, and 0/10. She reported complete resolution of light sensitivity and blurry vision. Total administration time was approximately fifteen minutes. At thirty minutes post-administration, her VAS was 0/10 and was 0/10 at four hours post-administration and 1/10 at twenty-four hours post-administration. There was no incidence of vertigo, nystagmus or aberrant autonomic response.

EXAMPLE 13

Patient number thirteen was a right-handed, 15-year-old female. Her history of migraine included six years of recurrent migraine. She would experience migraine headaches approximately twelve days per month. She reported 'moderate' impact on quality of life due to her migraines. Her current use of pharmacological agents for migraine included amitriptyline. Previous MRI showed no abnormalities. Pre-administration neurologic exam was essentially normal. She reported that her headache was generally subsiding, but that there was some residual pain and mild nausea. She stated that the current headache had been present for approximately four days and encompassed both sides of her head. On questioning, she reported that she had taken ibuprofen approximately six hours previous. Her pre-administration rating of pain on a VAS was 3/10.

Although she was experiencing pain on both sides of her head, she reported that she would typically experience more pain on the right side. She was administered the inventive method to the right ear. Over successive rounds of administration of the inventive method, her VAS scores pertaining to pain were 3/10, 2.5/10, and 0/10. Total administration time was approximately ten minutes. At thirty minutes post-administration, her VAS was 0/10 and was 0/10 at four hours post-administration and 0/10 at twenty-four hours post-administration. There was no incidence of vertigo, nystagmus or aberrant autonomic response.

The results obtained by use of the inventive method evidence that that migraine or headache may not be exclusively the result of vascular dysfunction, but may be propagated and maintained in part, through dysfunction of the trigeminocervical system. Embodiments of the inventive method may modulate that system by way of trigeminal afferents from the tympanic membrane (22). This particular pathway might have a unique and unexpected affinity for influencing aberrant patterns of brainstem activity and integration.

As can be easily understood from the foregoing, the basic concepts of the present invention may be embodied in a variety of ways. The invention involves numerous and varied embodiments of a method for external ear canal pressure regulation to alleviate disorder symptoms, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of an "adjustment" should be understood to encompass disclosure of the act of "adjusting"—whether explicitly discussed or not—and, conversely, were there effectively disclosure of the act of "adjusting", such a disclosure should be understood to encompass disclosure of an "adjustment" and even a "means for adjusting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the methods for external ear canal pressure regulation to alleviate disorder symptoms herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A method for treatment of a headache syndrome, comprising:
    providing a gas transfer device which generates a gas flow of a gas through an earplug, said earplug having an earplug external surface configured to sealably engage anexternal ear canal wall as a barrier between an external ear canal pressure and an ambient pressure; and
    treating a subject having said headache syndrome by:
        sealably engaging said earplug with said external ear canal wall; and
        operating said gas transfer device to generate said gas flow of said gas through said earplug to achieve an external ear canal pressure differential between said external ear canal pressure and said ambient pressure;
        operating said gas transfer device to change the external ear canal pressure differential between a positive external ear canal pressure differential and a negative external ear canal pressure differential, while the earplug is sealably engaged with the external ear canal wall;
        wherein said changing external ear canal pressure differential is effective to treat said headache syndrome.

2. The method of claim 1, wherein said gas comprises air.

3. The method of claim 1, wherein said change comprises oscillating said external ear canal pressure differential between said positive external ear canal pressure differential and said negative external ear canal pressure differential.

4. The method of claim 1, further comprising moving a tympanic membrane in response to achieving said external ear canal pressure differential between said external ear canal pressure and said ambient pressure.

5. The method of claim 1, wherein said headache syndrome comprises a migraine headache.

6. The method of claim 1, further comprising operating said gas transfer device to oscillate a pressure amplitude to generate a pressure wave having a pressure wave frequency.

7. A method for treatment of a headache syndrome, comprising:
    providing a fluid transfer device which generates a fluid flow of a fluid through an earplug, said earplug having an earplug external surface configured to sealably engage an external ear canal wall as a barrier between an external ear canal pressure and an ambient pressure; and
    treating a subject having said headache syndrome by:
        sealably engaging said earplug with said external ear canal wall;
        operating said fluid transfer device to generate said fluid flow of said fluid through said earplug to achieve an external ear canal pressure differential between said external ear canal pressure and said ambient pressure;
        operating said fluid transfer device to change the external ear canal pressure differential between a positive external ear canal pressure differential and a negative external ear canal pressure differential, while the earplug is sealably engaged with the external ear canal wall; and wherein said changing external ear canal pressure differential is effective to treat said headache syndrome.

8. The method of claim 7, wherein said change comprises oscillating between said positive external ear canal pressure differential and said negative external ear canal pressure differential.

9. The method of claim 7, further comprising moving a tympanic membrane in response to achieving said external ear canal pressure differential between said external ear canal pressure and said ambient pressure.

10. The method of claim 7, wherein said headache syndrome comprises a migraine headache.

11. The method of claim 7, further comprising operating said fluid transfer device to oscillate a pressure amplitude to generate a pressure wave having a pressure wave frequency.

12. A method for alleviating pain resulting from a headache syndrome, comprising:
providing a fluid transfer device which generates a fluid flow of a fluid through an earplug, said earplug having an earplug external surface configured to sealably engage an external ear canal wall as a barrier between an external ear canal pressure and an ambient pressure; and
treating a subject having said headache syndrome by:
sealably engaging said earplug with said external ear canal wall; and
operating said fluid transfer device to generate said fluid flow of said fluid through said earplug to achieve an external ear canal pressure differential between said external ear canal pressure and said ambient pressure;
operating said fluid transfer device to change the external ear canal pressure differential between a positive external ear canal pressure differential and a negative external ear canal pressure differential, while the earplug is sealably engaged with the external ear canal wall; and
wherein said changing external ear canal pressure differential is effective to alleviate said pain.

13. The method of claim 12, wherein said change comprises oscillating between said positive external ear canal pressure differential and said negative external ear canal pressure differential.

14. The method of claim 2, further comprising moving a tympanic membrane in response to achieving said external ear canal pressure differentials between said external ear canal pressure and said ambient pressure.

15. The method of claim 12, further comprising modulating a temperature of the ear.

* * * * *

UNITED STATES PATENT AND TRADEMARK OFFICE
CERTIFICATE OF CORRECTION

PATENT NO. : 10,251,790 B2  
APPLICATION NO. : 14/292469  
DATED : April 9, 2019  
INVENTOR(S) : David Mager George et al.

Page 1 of 1

It is certified that error appears in the above-identified patent and that said Letters Patent is hereby corrected as shown below:

On the Title Page

On Page 5, Column 1, Item (56), Line 36, under Other Publications, change "www.tmjtreatmentse.com," to --www.tmjtreatmentsc.com,--.

In the Specification

In Column 3, Line 64, change "fluidicly" to --fluidically--.

In Column 8, Line 45, change "mechanioreceptive" to --mechanoreceptive--.

In Column 11, Line 37, change "fluidicly" to --fluidically--.

In Column 16, Line 13, change "topiromate," to --topiramate,--.

In Column 17, Line 20, change "topiromate" to --topiramate--.

In Column 19, Line 6, change "venlaxafine" to --venlafaxine--.

In Column 19, Line 8, change "butalibital/floricet," to --butalbital/fioricet,--.

In Column 19, Line 64, change "that that" to --that--.

In the Claims

In Column 22, Line 12, Claim 1, change "anexternal" to --an external--.

In Column 24, Line 19, Claim 14, change "claim 2," to --claim 12,--.

Signed and Sealed this  
Ninth Day of July, 2019

Andrei Iancu  
*Director of the United States Patent and Trademark Office*